(12) United States Patent
Igarashi et al.

(10) Patent No.: US 8,658,037 B2
(45) Date of Patent: Feb. 25, 2014

(54) METHOD FOR DETERMINING PHYSIOLOGICAL STATE OF MICROBIAL COMMUNITY AND WASTEWATER TREATMENT METHOD

(75) Inventors: Ryoji Igarashi, Ichihara (JP); Takuji Yamamoto, Ichihara (JP)

(73) Assignee: Seiko PMC Corporation, Tokyo (JP)

( * ) Notice: Subject to any disclaimer, the term of this patent is extended or adjusted under 35 U.S.C. 154(b) by 214 days.

(21) Appl. No.: 13/002,498

(22) PCT Filed: Jul. 3, 2009

(86) PCT No.: PCT/JP2009/062210
§ 371 (c)(1),
(2), (4) Date: Jan. 3, 2011

(87) PCT Pub. No.: WO2010/004938
PCT Pub. Date: Jan. 14, 2010

(65) Prior Publication Data
US 2011/0100903 A1    May 5, 2011

(30) Foreign Application Priority Data

Jul. 11, 2008  (JP) ................................ 2008-181440

(51) Int. Cl.
*C02F 3/00*    (2006.01)
*B01D 35/00*   (2006.01)
*C12Q 1/02*    (2006.01)
*G01N 33/48*   (2006.01)

(52) U.S. Cl.
USPC ............ 210/614; 210/610; 210/85; 210/745; 435/29; 702/19

(58) Field of Classification Search
None
See application file for complete search history.

(56) References Cited

U.S. PATENT DOCUMENTS 5,858,222 A  * 1/1999 Shibata et al. ................. 210/177
2007/0272615 A1* 11/2007 Batista ........................... 210/670

FOREIGN PATENT DOCUMENTS

| CN | 1425074 | 6/2003 |
| CN | 1434285 | 8/2003 |

(Continued)

OTHER PUBLICATIONS

Ziglio et al.; "Assessment of activated sludge viability with flow cytometry"; 2002; Pergamon; Water Research 36; 460-468.*

(Continued)

*Primary Examiner* — Nam Nguyen
*Assistant Examiner* — Richard Gurtowski
(74) *Attorney, Agent, or Firm* — Knobbe Martens Olson & Bear LLP

(57) ABSTRACT

The present invention provides a method for determining the physiological state of a microbial community, which rapidly and precisely determines the physiological state of a microbial community present in a treatment tank of a wastewater biological treatment facility; and a wastewater treatment method utilizing the same. In the method for determining the physiological state of a microbial community of the present invention, the method includes the steps of staining the microbial community collected from a treatment tank of a wastewater biological treatment facility with a first fluorescent dye which binds to a nucleotide chain of a microbe in the microbial community, and a second fluorescent dye which is degraded by an enzyme in cells of the microbe to emit fluorescent light having a wavelength different from that of the first fluorescent dye; measuring a first fluorescent intensity (F1) derived from the first fluorescent dye and a second fluorescent intensity (F2) derived from the second fluorescent dye, regarding the stained microbial community; and determining the satisfactory degree of the physiological state of the microbial community.

17 Claims, 21 Drawing Sheets

(56) References Cited

FOREIGN PATENT DOCUMENTS

| JP | H02-031892 | 2/1990 |
|---|---|---|
| JP | 2003-284592 | 10/2003 |
| JP | 2006-238771 A | 9/2006 |
| JP | 2007-097532 | 4/2007 |
| JP | 2008-099625 | 5/2008 |

OTHER PUBLICATIONS

Selinummi et al.; "Software for quantification of labeled bacteria from digital microscope images by automated image analysis"; Dec. 2005; Biotechniques 39; 859-863.*

Kanagawa, T., "An Overview of Microbial Community Analysis of Activated Sludge by Molecular Methods," Journal of Water and Waste, vol. 48, No. 1, pp. 48-52 (2006).

Ziglio et al., "Assessment Of Sludge Viability With Flow Cytometry," Water Research, 2002, vol. 36, pp. 460-468.

Rault et al., "Multiparametric Cytometry Allows Rapid Assessment Comparison of Lactic Acid Bacteria After Freezing and During Frozen Storage," Cryobiology, 2007, vol. 55, pp. 35-43.

Papadimitriou, K., "Assessment of the Physiological *Streptococcus macedonicus* Fluoroscene Probes," Int. J. Food Microbiol., 2006, vol. 111, pp. 197-205.

Menendez-Vega Demelza et al., "Engineered in situ bioremediation of soil and groundwater polluted with weathered hydrocarbons," European Journal of Soil Biology, 2007, vol. 43, pp. 310-321.

Amor Ben Kaouther et al., "Multiparametric Flow Cytometry and Cell Sorting for the Assessment of Viable, Injured, and Dead Bifidobacterium Cells during Bile salt Stress," Appl. Environ. Microbiol., 2002, vol. 68, No. 11, pp. 5209-5216.

Bunthof J. Christine et al., "Flow Cytometric Assessment of Viablity of Lactic Acid Bacteria," Appl. Environ. Microbiol., 2001, vol. 67, No. 5, pp. 2326-2335.

International Search Report issued in corresponding PCT Application No. PCT/JP2009/062210, mailed Sep. 8, 2009.

Ziglio, et al., "Assessment Of Activated Sludge Viability With Flow Cytometry," Water Research, (2002), vol. 36, pp. 460-468.

Rault, et al., "Multiparametric Flow Cytometry Allows Rapid Assessment and Comparison of Lactic Acid Bacteria Viability After Freezing and During Frozen Storage," Cryobiology, (2007), vol. 55, pp. 35-43.

Papadimitriou, K., et al, "Rapid Assessment of the Physiological Status of *Streptococcus macedonicus* by Flow Cytometry and Fluorescene Probes," Int. J. Food Microbiol. (2006), vol. 111, pp. 197-205.

Office Action mailed Oct. 9, 2012 in corresponding Chinese Patent Application No. 200980126463.X.

* cited by examiner

US 8,658,037 B2

METHOD FOR DETERMINING PHYSIOLOGICAL STATE OF MICROBIAL COMMUNITY AND WASTEWATER TREATMENT METHOD

RELATED APPLICATIONS

This application is the U.S. National Phase filing under 35 U.S.C. §371 of PCT/JP2009/062210, filed Jul. 3, 2009, which designated the United States and was published in a language other than English, which claims priority under 35 U.S.C. §119(a)-(d) to Japanese Patent Application No. 2008-181440, filed Jul. 11, 2008, the entire content of which is incorporated herein by reference.

TECHNICAL FIELD

The present invention relates to a method for determining the physiological state of a microbial community, which rapidly and precisely determines the physiological state of a microbial community present in a treatment tank of a wastewater biological treatment facility. The present invention further relates to a method for treating wastewater, which can stably perform a wastewater treatment while maintaining and managing the physiological state of a microbial community satisfactorily, based on the physiological state of a microbial community determined by the determination method. The present invention can apply to a treatment tank of various wastewater treatment facilities such as an aeration tank of a wastewater treatment facility by an activated sludge process, and a reaction tank of a wastewater treatment facility by a biofilm method.

BACKGROUND ART

In a wastewater treatment facility by an activated sludge process, while air is supplied to a treatment tank containing an activated sludge (aeration tank), wastewater to be biologically treated is supplied to the treatment tank, a microbial community forming an activated sludge and wastewater are contacted under the aerobic environment, a microbial community takes up nutrient components in wastewater, and proliferates, thereby, organic pollution in wastewater is decreased. Wastewater that flows out from the treatment tank is guided to a precipitation tank to settle a sludge, and is separated from treated water. In such a wastewater treatment process by an activated sludge process, many kinds of microbes are present together in the treatment tank, and they form a sludge flock, and are floated and suspended in water in the aeration tank in many cases.

In this kind of wastewater treatment facility, in order to perform treatment in the stable state for a long period of time, it is required to grasp and manage the physiological state of a microbial community present in the treatment tank.

An example of the case where the physiological state of a microbial community in the treatment tank is unsatisfactory includes the case where a sludge flock becomes bulky and cotton-like, reducing a difference in a specific gravity between water, consolidation property of the sludge flock is reduced in the precipitation tank, and bulking occurs, in which separation between treating water and the sludge flock becomes difficult. When this bulking is generated, since it becomes difficult to separate treated water and the activated sludge in the precipitation tank, an operation efficiency of the wastewater treatment facility is extremely reduced.

In order to prevent this bulking, it is necessary to precisely grasp the physiological state of a microbial community present in the treatment tank, and take any strategy so that a bulking causal bacterium such as a filamentous bacterium does not predominantly proliferate.

However, a method for determining the physiological state of a microbial community which is effective in rapidly and precisely determining the physiological state of a microbial community present in the treatment tank has not previously been established, and it was difficult to prevent inconvenience such as bulking etc. in advance.

As a method for determining the physiological state of a microbe, for example, the prior art described in Patent Documents 1 to 3 has hitherto been proposed.

Patent Document 1 discloses a method of staining-treating a specimen containing a microbe using a first fluorescent dye, a second fluorescent dye having a wavelength which is different from a wavelength of the first fluorescent dye, and a third fluorescent dye having a wavelength which is different from wavelengths of the first and second fluorescent dyes, measuring fluorescent light with flow cytometry or a laser scanning cytometer, and grasping, from the result, the cell number, the environmental polluting compound cleaning activity and the survival state of a microbe which can clean the environmental polluting compound in the specimen by degradation, dechlorination etc.

Patent Document 2 discloses a method for determining the physiological activity of a microbe, which includes trapping a microbe on a filtration membrane, culturing the microbe, and staining the microbe on the filtration membrane with a fluorescent staining solution which has been permeated from a lower surface side of the filtration membrane.

Patent Document 3 discloses a method for analyzing a cell cycle, which includes the steps of visualizing a cell nucleus, a step of visualizing a biological molecule which is specifically expressed in a specified cell cycle, and identifying a ratio of the specified cell cycle in a cell population utilizing numerical value data of the cell nucleus obtained by visualizing the cell nucleus, and numerical value data of the biological molecule obtained by visualizing the biological molecule.

In addition, as a method of controlling the step of activated sludge-type wastewater treating, Patent Document 4 discloses the step of controlling an aerobic activated sludge-type wastewater treating step, comprising measuring an amount of a fluorescently labeled microbe with flow cytometry by binding a microbe to a fluorescently labeled antibody to this microbe, or converting a fluorogen substrate by the specific metabolism ability of the microbe, in a typical sample from an activated sludge and/or an inlet of an activated sludge tank, upon continuous monitoring of an amount of one kind or several kinds of microbes, regarding the microbes which appear most frequently in an activated sludge and, at the same time, measuring a total amount of microbes present in the sample by scattered light and/or DNA staining, and monitoring an amount of the microbe by regulating an amount of one kind or several kinds of specified microbes and/or the growth condition of the microbes, in response to the thus obtained measured value.

PRIOR ART DOCUMENTS

Patent Documents

[Patent Document 1] Japanese Patent Laid-Open Publication No. 2003-284592
[Patent Document 2] Japanese Patent Laid-Open Publication No. 2007-97532

[Patent Document 3] Japanese Patent Laid-Open Publication No. 2008-99625

[Patent Document 4] Japanese Patent Laid-Open Publication No. Hei 2-31892

Non-Patent Document

[Non-Patent Document 1] Journal of Water and Waste, Vol. 48, No. 1, p 48-52

DISCLOSURE OF THE INVENTION

Problems to be Solved by the Invention

However, the prior art disclosed in Patent Documents 1 to 3 is not for determining the physiological state of a microbial community present in a treatment tank of a wastewater biological treatment facility. In addition, there is no description regarding determination of whether the state of a microbial community present in the treatment tank of the wastewater biological treatment facility is satisfactory or unsatisfactory in terms of the physiological state. Therefore, from the prior art, a method for determining the physiological state of a microbial community present in the treatment tank of the wastewater biological treatment facility cannot be conceived.

In the prior art disclosed in Patent Document 4, one kind or several kinds of main microbes to be controlled are selected among microbes isolated from an activated sludge by a pure culturing method.

However, today, it is known that 90% or more (see, for example, Non-Patent Document 1), specifically 90 to 99% of microbes (bacteria) in the environment cannot be purely cultured by a general medium.

According to the result of micobial flora analysis of an activated sludge by a molecular biological procedure, although many kinds of various bacteria are present in an activated sludge, a specified kind is not particularly major, and it is known that bacteria different from the previously known bacteria are present in a particularly large number (see, for example, Non-Patent Document 1).

In addition, Patent Document 4 discloses that regulation or improvement of the growth condition for a specified microbe or a microbe which converts a fluorogen substrate in the microbe by the enzyme activity can be performed by regulating a supply amount of a nutrient, a pH value and/or a temperature, but does not disclose the condition which is specific to such an extent that a person skilled in the art can implement.

Further, Patent Document 4 describes that life and death of a bacterium can be determined by esterase activity and permeability into a cell, by staining with carboxyfluorescein diacetate, which is a fluorogen substrate, and propidium iodide, but this is the known technique.

In addition, in Patent Document 4, what improvement is obtained in activated sludge treatment by monitoring and controlling these microbes has not been revealed.

As is apparent from the above description, the prior art disclosed in Patent Document 4, in which one kind or several kinds of microbes obtained by pure culturing are monitored and controlled, is insufficient as a method of controlling activated sludge treatment.

The present invention was conceived in view of the aforementioned circumstances, and an object thereof is to provide a method for determining the physiological state of a microbial community, which rapidly and precisely determines the physiological state of a microbial community present in a treatment tank of a wastewater biological treatment facility, and a wastewater treating method which can stably perform a wastewater treatment while maintaining and managing the physiological state of a microbe community satisfactorily, based on the physiological state of a microbial community determined by the determination method.

Means for Solving the Problems

In order to achieve the object, the present invention provides a method for determining the physiological state of a microbial community present in a treatment tank of a wastewater biological treatment facility, the method comprising:

collecting the microbial community present in the treatment tank;

staining the microbial community with a first fluorescent dye which binds to a nucleotide chain of a microbe of the microbial community, and a second fluorescent dye which is degraded by an enzyme in cells of the microbe to emit fluorescent light having a wavelength different from that of the first fluorescent dye;

measuring a first fluorescent intensity (F1) derived from the first fluorescent dye and a second fluorescent intensity (F2) derived from the second fluorescent dye, regarding the stained microbial community; and determining that the physiological state of the microbial community is satisfactory when a value of a ratio (F1/F2) of the first fluorescent intensity (F1) and the second fluorescent intensity (F2) is equal to or more than a preset standard value, and determining that the physiological state of the microbial community is unsatisfactory when the value of a ratio (F1/F2) is lower than the standard value.

In the method for determining the physiological state of a microbial community of the present invention, the first fluorescent dye can be one kind selected from the group consisting of propidium iodide, ethidium bromide, ethidium homodimer, DAPI, 7-aminoactinomycin D and SYTOX Green, and the second fluorescent dye can be one kind selected from the group consisting of fluorescein diacetate, carboxyfluorescein diacetate, sulfofluorescein diacetate, dichlorofluorescein diacetate, calcein-AM and CFSE.

In the method for determining the physiological state of a microbial community of the present invention, the measuring of a fluorescent intensity can be performed by fluorescent microscopy observation or analysis using a flow cytometer of the stained microbial community.

In the method for determining the physiological state of a microbial community of the present invention, the measuring a fluorescent intensity can be performed by observing the stained microbial community with a fluorescent microscope, digitalizing fluorescent light derived from the first fluorescent dye and the second fluorescent dye as a signal area based on a preset threshold of a signal intensity, by use of an image processing software for an image of the fluorescent microscopy observation, and determining a value of a ratio of each signal area derived from the first fluorescent dye and the second fluorescent dye.

In the method for determining the physiological state of a microbial community of the present invention, the measuring of a fluorescent intensity can be also performed by observing the stained microbial community with a fluorescent microscope, calculating a luminance and a signal area regarding an image of the fluorescent microscopy observation by use of an image processing software, digitalizing a total fluorescence amount (=signal area×luminance) derived from a fluorescent dye, and determining a value of a ratio of the total fluorescence amount derived from the first fluorescent dye to the second fluorescent dye (S1/S2).

In the method for determining the physiological state of a microbial community of the present invention, the measuring of a fluorescent intensity can be also performed by measuring first fluorescent intensity (F1) and the second fluorescent intensity (F2) of the stained microbial community by use of a flow cytometer, and determining a value of a ratio of the first fluorescent intensity (F1) and the second fluorescent intensity (F2) (F1/F2).

In the method for determining the physiological state of a microbial community of the present invention, it is preferable that when the value of a ratio (F1/F2) of the first fluorescent intensity (F1) to the second fluorescent intensity (F2) is within a range of 1 to 20, it is determined that the physiological state of the microbial community is satisfactory and, when the value of the ratio (F1/F2) is less than 1, or more than 20, it is determined that the physiological state of a microbial community is unsatisfactory.

The present invention provides a method for treating wastewater, comprising:

performing the method for determining the physiological state of a microbial community of the present invention; and performing, when the physiological state of the microbial community is determined to be unsatisfactory by determination in the determination method, (A) placing a microbial preparation into a treatment tank, and/or (B) controlling a solids retention time of a treatment tank, and performing wastewater treatment while adjusting the operation state of a treatment tank of a wastewater biological treatment facility so that the physiological state of a microbial community becomes satisfactory.

In the method for treating wastewater of the present invention, the (B) controlling of a solids retention time of a treatment tank can be performed by controlling the solids retention time of a treatment tank to be controlled to be within a solids retention time calculated by the following equation (1)±2 days:

$$\text{solids retention time (day)} = (\tau \times X)/((a \times Ci) + (b \times Si) - (c \times \tau \times X)) \quad (1)$$

[wherein each symbol in the equation (1) has the following meaning:

τ: hydraulic retention time of reaction tank V/Qi (days)
Qi: wastewater amount (m$^3$/day)
Ci: soluble BOD value of wastewater (mgO/L)
Si: SS concentration of wastewater (mg/L)
X: MLSS in reaction tank (mg/L)
V: reaction tank volume (m$^3$)
a: sludge conversion rate relative to soluble BOD (gMLSS/gBOD)
b: sludge conversion rate relative to SS (gMLSS/gSS)
c: coefficient representing reduction amount due to endogenous respiration of activated sludge microbe (L/day)].

Effect of the Invention

The method for determining the physiological state of a microbial community of the present invention can rapidly and precisely determine whether or not the physiological state of a microbial community present in the treatment tank of the wastewater biological treatment facility is satisfactory.

The method for treating wastewater of the present invention can stably perform a wastewater treatment while maintaining and managing the physiological state of a microbial community satisfactorily, based on the physiological state of a microbial community determined by the determination method of the present invention.

BEST MODE FOR CARRYING OUT THE INVENTION

Figure 1:
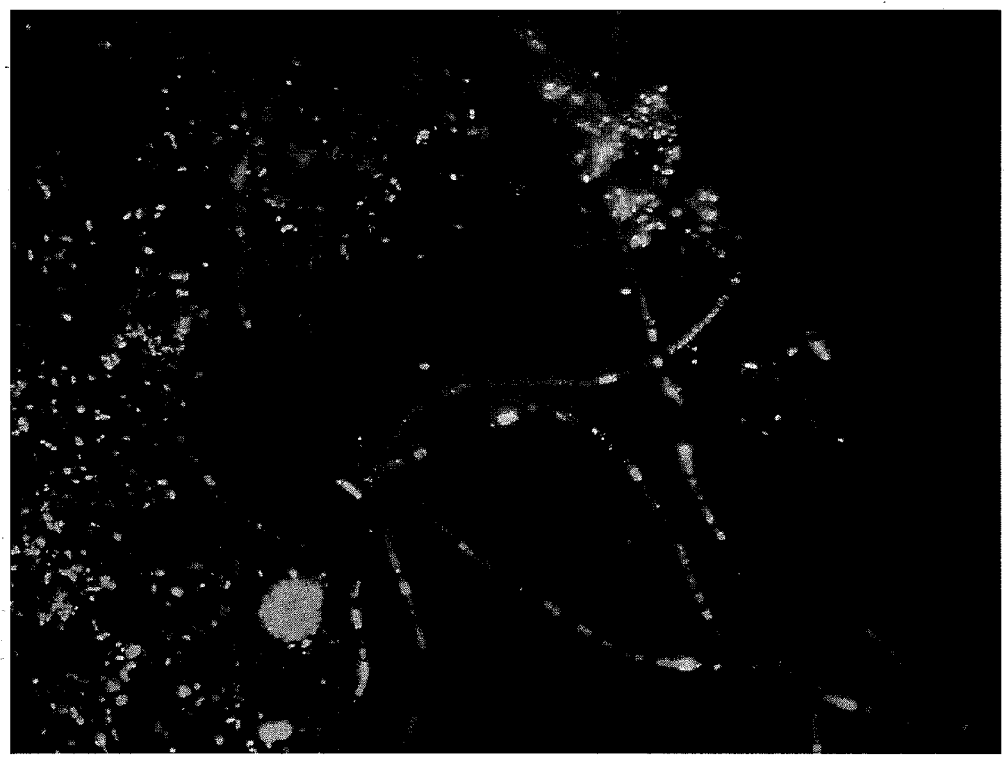
FIG. 1 is a CFDA fluorescent image of a sample before the addition of a microbial preparation in Example 1.

An activated sludge, when its constituent microbial community is in a logarithmic proliferation phase (high proliferation activity, high BOD load, short solids retention time), is unsatisfactory in treated water quality and solid liquid separation and, when in a stationary phase (little proliferation, standard load, suitable solids retention time), is satisfactory in treated water quality and solid liquid separation.

The present inventors continued to intensively study a method for determining the physiological state of a microbial community present in a treatment tank of a wastewater biological treatment facility and, as a result, confirmed that, when using permeability into a cell membrane as an index, a sludge flock collected from the treatment tank is double-stained with a first fluorescent dye which binds to a nucleotide chain of a microbe in the microbial community, and a second fluorescent dye which is degraded by an enzyme in a microbe cell to emit fluorescent light having a wavelength different from that of the first fluorescent dye, and this is observed with a fluorescent microscope; bacteria in the dispersion proliferation state, which is a cause for bulking, and a filamentous bacterium in proliferation are stained mainly with a second fluorescent dye, therefore fluorescent light derived from the second fluorescent dye is more intensively observed than fluorescent light derived from the first fluorescent dye, in a sludge flock which has caused bulking. On the other hand, it was confirmed that when a sludge flock collected from the treatment tank which did not cause bulking, and was determined to be in the satisfactory operation state is similarly double-stained, and observed with a fluorescent microscope; fluorescent light derived from the first fluorescent dye is more intensively observed than fluorescent light derived from the second fluorescent dye.

The present inventors further found out that, regarding the stained microbial community, when a first fluorescent intensity (F1) derived from the first fluorescent dye, and a second fluorescent intensity (F2) derived from the second fluorescent dye are measured, and the resulting measured values are compared with a preset standard value, when a value of a ratio of the first fluorescent intensity (F1) to the second fluorescent intensity (F2) of measured valued (F1/F2) is equal to or more than the standard value, it is determined that the physiological state of a microbial community is satisfactory and, when the value of a ratio (F1/F2) is less than the standard value, it is determined that the physiological state of a microbial community is unsatisfactory, thereby, whether the physiological state of a microbial community present in the treatment tank is satisfactory or not can be rapidly and precisely determined. Further, it was found out that when a whole sludge flock is double-stained with the first fluorescent dye and the second fluorescent dye, and a value of a ratio of first fluorescent intensity (F1) to second fluorescent intensity (F2) (F1/F2) is 1 or more, satisfactory treated water quality and solid liquid separation are obtained, resulting in completion of the present invention.

That is, the method for determining the physiological state of a microbial community of the present invention is a method for determining the physiological state of a microbial community present in a treatment tank of a wastewater biological treatment facility, the method comprising:

collecting the microbial community present in the treatment tank;

staining the microbial community with a first fluorescent dye which binds to a nucleotide chain of a microbe in the microbial community, and a second fluorescent dye which is degraded with an enzyme in a cell of the microbe to emit fluorescent light having a wavelength different from that of the first fluorescent dye;

measuring a first fluorescent intensity (F1) derived from the first fluorescent dye and a second fluorescent intensity (F2) derived from the second fluorescent dye, regarding the stained microbial community;

determining that the physiological state of a microbial community is satisfactory when a value of a ratio (F1/F2) of first fluorescent intensity (F1) and the second fluorescent intensity (F2) is equal to or more than a preset standard value, and determining that the physiological state of the microbial community is unsatisfactory when the value of a ratio (F1/F2) is lower than the standard value, regarding measured values obtained in the above step.

Herein, the value of a ratio of the first fluorescent intensity (F1) to the second fluorescent intensity (F2) (F1/F2) can be regarded as a value of a ratio of a bacterium in which a cell membrane has complete proliferating property, relative to a bacterium in which a cell membrane has incomplete non-proliferating property, in a sludge flock for which the physiological state is determined.

Generally, in order to control an activated sludge proliferation phase such as a logarithmic proliferation phase and a stationary phase, a solids retention time is used as a parameter.

Since a suitable solids retention time is different depending on a treatment facility, water quality of wastewater, and treatment environment, an optimal solids retention time can be found out by operating a solids retention time based on the fluorescent staining result, and it becomes possible to maintain activated sludge treatment with satisfactory treated water quality.

As the first fluorescent dye used in the present invention, a fluorescent reagent which binds to a nucleic acid in a cell based on permeability of a cell membrane is used. Specifically, the dye can be at least one kind selected from the group consisting of propidium iodide (hereinafter referred to as PI), a phenanthridium-based fluorescent reagent such as ethidium bromide, ethidium homodimer, DAPI, 7-aminoactinomycin D and SYTOX Green, and PI is particularly preferable.

In addition, as the second fluorescent dye, a fluorescent reagent exhibiting fluorescent property by the action of an enzyme in a cell is used. Specifically, the dye can be one kind selected from the group consisting of fluorescein diacetate (FDA), carboxyfluorescein diacetate (hereinafter referred to as CFDA), sulfofluorescein diacetate (SFDA), dichlorofluorescein diacetate (DCFDA), calcein-AM and CFSE, and CFDA is particularly preferable.

Furthermore, it is necessary that a wavelength region of fluorescent light derived from the first fluorescent dye, and a wavelength region of fluorescent light derived from the second fluorescent dye be different wavelength regions so that they can be clearly separated with a wavelength selection filter etc. and, also from this point, it is preferable to use PI as the first fluorescent dye, and use CFDA as the second fluorescent dye.

This first fluorescent dye permeates only when a cell membrane of a bacterium is incomplete, and the second fluorescent dye permeates when a cell membrane of a bacterium is complete or incomplete. By this action mechanism, the aforementioned determination becomes possible.

Generally, in the state where the integrity of a cell membrane of a bacterium is lost, the bacterium is interpreted to be dead, but from the result of investigation of many sludge flocks actually collected from the treatment tank by the present inventers, even in the case of an activated sludge in which a bacterium having an incomplete cell membrane is predominant, a BOD degradation rate is high, satisfactory treated water quality is obtained, and solid liquid separation is satisfactory and, thus, a possibility that a bacterium having an incomplete cell membrane in an activated sludge is alive, is suggested.

In addition, evidence that the respiration activity is high, and metabolism such as protein synthesis is performed in an activated sludge of an incomplete cell membrane has been obtained, and an activated sludge constructed of a bacterium having an incomplete cell membrane is not proliferated (less excess sludge), but is an ideal activated sludge which performs metabolism and respiration to degrade polluting substances.

The step of measuring a fluorescent intensity can be performed by observation with a fluorescent microscope of, or analysis using a flow cytometer of the stained microbial community.

When the step is performed, for example, by observation with a fluorescent microscope, the step can be performed by:
(a) a method of observing the stained microbial community, digitalizing fluorescent light derived from the first fluorescent dye and the second fluorescent dye as a signal area based on a preset threshold of a signal intensity, by use of an image processing software regarding an image of the fluorescent microscopy observation, and determining a value of a ratio of each signal area derived from the first fluorescent dye and the second fluorescent dye,
(b) a method of observing the stained microbial community with a fluorescent microscope, calculating a luminance and a signal area using an image processing software regarding an image of the fluorescent microscopy observation, digitalizing a total fluorescence amount (=signal area×luminance) derived from a fluorescent dye, and determining a value of a ratio of a total fluorescence amount derived from the first fluorescent dye and the second fluorescent dye ($S1/S2$).

In the methods of (a) and (b), a signal area or a total fluorescence amount derived from the first fluorescent dye becomes a first fluorescent intensity ($F1$), a signal area or a total fluorescence amount derived from the second fluorescent dye becomes a second fluorescent intensity ($F2$), and a value of a ratio of them ($F1/F2$) is calculated.

In the methods of (a) and (b), in order to digitalize the fluorescent intensity ($F1$) derived from the first fluorescent dye, and the fluorescent intensity ($F2$) derived from the second fluorescent dye, for example, the following procedure can be used.

The double-stained microbial community (hereinafter sometimes referred to as sample) is observed with a fluorescent microscope. Fluorescent light derived from the fist fluorescent dye (hereinafter referred to as first fluorescent light) is inspected through a filter transmitting a wavelength region of this fluorescent light, and fluorescent light derived from the second fluorescent dye (hereinafter referred to as second fluorescent light) is inspected through a filter transmitting a wavelength region of this fluorescent light. A fluorescent microscope image of each of the first fluorescent light and the second fluorescent light is taken, each fluorescent microscopy observation image is binarization-processed using an image processing software, and each signal region is digitalized as an area (pixel) and a total fluorescence amount (pixel×luminance).

The obtained numerical value is calculated as "signal area of first fluorescent light/signal area of second fluorescent light" and "total fluorescence amount of first fluorescent light/total fluorescence amount of second fluorescent light", and a value of each ratio is obtained.

In addition, when a flow cytometer is used, a first fluorescent intensity ($F1$) and a second fluorescent intensity ($F2$) of a double-stained sample are measured using a flow cytometer, and a value of a ratio of the first fluorescent intensity ($F1$) to the second fluorescent intensity ($F2$) ($F1/F2$) is obtained, and thus digitalization can be performed.

In the method for determining the physiological state of a microbial community of the present invention, when the physiological state of a microbial community of the treatment tank is determined based on the value of a ratio of the first fluorescent intensity ($F1$) to the second fluorescent intensity ($F2$) ($F1/F2$), a standard value thereof can be appropriately changed depending on a size and the operation circumstances (a kind, an amount, a BOD concentration etc. of wastewater) of the treatment tank to be determined, but usually the value of a ratio of the first fluorescent intensity ($F1$) to the second fluorescent intensity ($F2$) ($F1/F2$) of 1.0 is used as a standard and, when the value of a ratio ($F1/F2$) is less than 1.0, it can be determined that the physiological state of a microbial community is unsatisfactory and, when the value of a ratio ($F1/F2$) is more than 1.0, it can be determined that the physiological state of a microbial community is satisfactory. This value of a ratio (F1/F2) of the case where the state can be determined to be satisfactory is preferably within a range of 1 to 20.

The present invention provides a method for determining the physiological state of a microbial community present in a treatment tank of a wastewater biological treatment facility, and performing wastewater treatment while the operation state of the treatment tank is adjusted, so that the physiological state of a microbial community becomes satisfactory, based on the determination result.

Specifically, a method for treating wastewater is provided, said method comprising: determining the physiological state of a microbial community present in the treatment tank by the method for determining the physiological state of a microbial community of the present invention and, performing, when the physiological state of the microbial community is unsatisfactory, either or both of:

(A) placing a microbial preparation into the treatment tank,
(B) controlling a solids retention time of the treatment tank while adjusting the operation state of the treatment tank, so that the physiological state of a microbial community becomes satisfactory.

Examples of the microbial preparation used in the (A) include trade names MC-003, MC-004, MC-005, MC-008, MC-038, and MC-Cap of SEIKO PMC CORPORATION.

In addition, when the (B) controlling of a solids retention time of the treatment time is performed, the controlling can be performed by controlling so that the solids retention time of the treatment tank to be controlled is within a solids retention time calculated by the following equation (1) ±2 days:

$$\text{solids retention time (day)} = (\tau \times X)/((a \times Ci) + (b \times Si) - (c \times \tau \times X)) \quad (1)$$

[wherein each symbol in the equation (1) has the following meaning:
$\tau$: hydraulic retention time of reaction tank V/Qi (day)
Qi: wastewater amount (m$^3$/day)
Ci: soluble BOD value of wastewater (mgO/L)
Si: SS concentration of wastewater (mg/L)
X: MLSS in reaction tank (mg/L)
V: reaction tank volume (m$^3$)
a: sludge conversion rate relative to soluble BOD (gMLSS/gBOD)
b: sludge conversion rate relative to SS (gMLSS/gSS)
c: coefficient representing reduction amount due to endogenous respiration of activated sludge microbe (L/day)].

The effects of the present invention will be proved below by way of examples.

Meanings of terms used in the following Examples are as follows.

"A solids retention time is a period of time for an activated sludge to be present in a treatment tank.

"COD reduction rate improved value" is the value (unit: %) obtained by subtracting a COD reduction rate of wastewater before a test from a COD reduction rate of wastewater after a test. The plus value means that the COD reduction rate is improved compared with that before the test.

"SVI" is the volume (ml) occupied by 1 g of an activated sludge and means the degree of bulking of the activated sludge.

"SVI improved value" is the value (unit: ml/g) obtained by subtracting SVI before a test from SVI after a test. The minus value means that SVI is improved compared with that before the test.

"Transparency" is the liquid level which enables visual observation of double-cross in the bottom of a measuring cylinder. The value of 30 cm or more is a rough estimate of satisfactory transparency.

"SV30" is the value obtained by placing an activated sludge in a container, standing for 30 minutes, and expressing the settled sludge volume by a percentage relative to the total amount of the activated sludge.

"SV30 improved value" is the value obtained by subtracting SV30 before a test from SV30 after a test. The minus value means that SV30, namely, settleability of an activated sludge is improved compared with that before the test.

Example 1

Improved Example by the Addition of Microbial Preparation to Activated Sludge System In an activated sludge treatment facility of industrial wastewater, for the purpose of improving bulking (SVI value) of the activated sludge, a measure was taken by the addition of a microbial preparation based on an image of fluorescent microscopy observation of a sludge constituting-microbial community.

The volume load of the target activated sludge treatment facility is 1.4 kg-BOD/m$^3$/day.

[Fluorescent Staining of Activated Sludge]

An activated sludge sample collected through an aeration tank outlet of this activated sludge treatment facility was subjected to double staining using PI (final concentration: 1 mg/L) as a first fluorescent dye and CFDA (final concentration: 10 mg/L) as a second fluorescent dye.

As PI and CFDA, the following were used.
PI (Propidium iodide, manufactured by Wako Pure Chemical Industries, Ltd., 160-16723).
CFDA (6-Carboxyfluorescein diacetate, manufactured by Sigma, C5041).

[Determination of the Physiological State of Sludge-Constituting Microbial Community Based on Fluorescent Microscopy Observation]

Using a fluorescent microscope (fluorescent microscope BX51, manufactured by OLYMPUS CORPORATION), the above sample was observed, and fluorescent images of PI and CFDA were taken at a magnification of 400 times.

Fluorescence observation of PI was performed using a mirror unit: U-MWIG3, an excitation filter: BP-530-550 and an absorption filter: BA575IF.

Fluorescence observation of CFDA was performed using a mirror unit: U-MNIBA3, an excitation filter: BP-470-495 and an absorption filter: BA510-550.

The images thus taken were subjected to binarization processing using an image analysis software (WinRoof, manufactured by MITANI CORPORATION), and each signal area was digitalized as an area (pixel) and a total fluorescence amount (pixel×luminance).

The obtained numerical values were calculated as "PI signal area/CFDA signal area" and "PI total fluorescence amount/CFDA total fluorescence amount" and the value of each ratio was determined. When the value of the ratio is 1.0 as a border or more, the physiological state of the constituting microbial community of the activated sludge is satisfactory. When the value of the ratio is less than 1.0, it is determined as a state where an improvement is required. Only the "PI signal area/CFDA signal area" will be described below.

Figure 2:
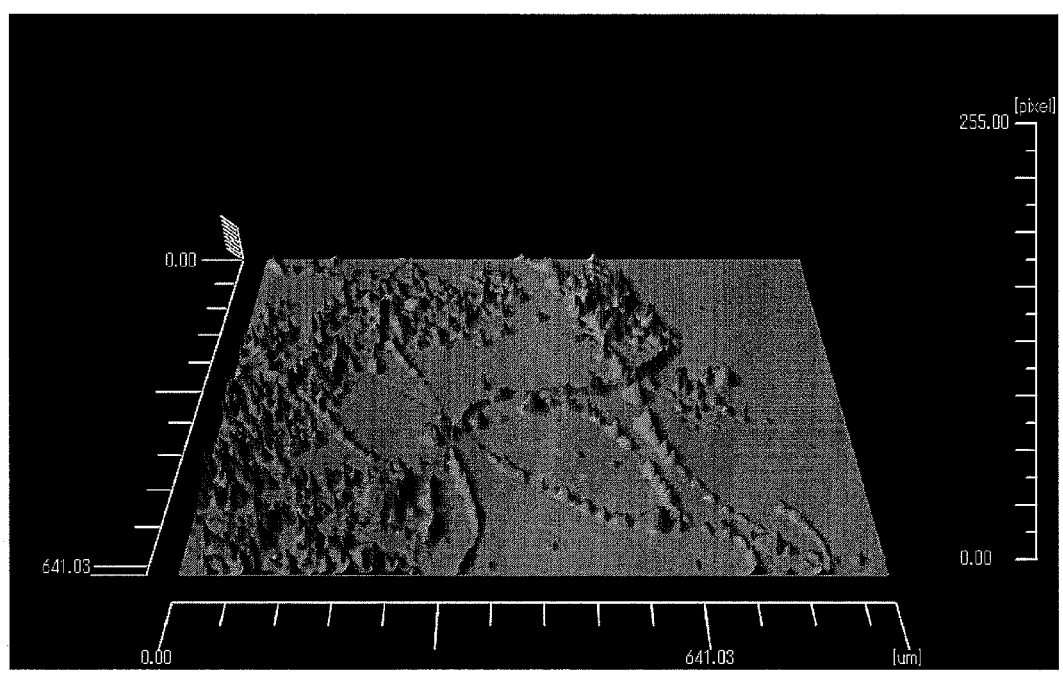
FIG. 2 is an image for the measurement of the total amount of CFDA fluorescence of the same sample used in FIG. 1.
Figure 3:
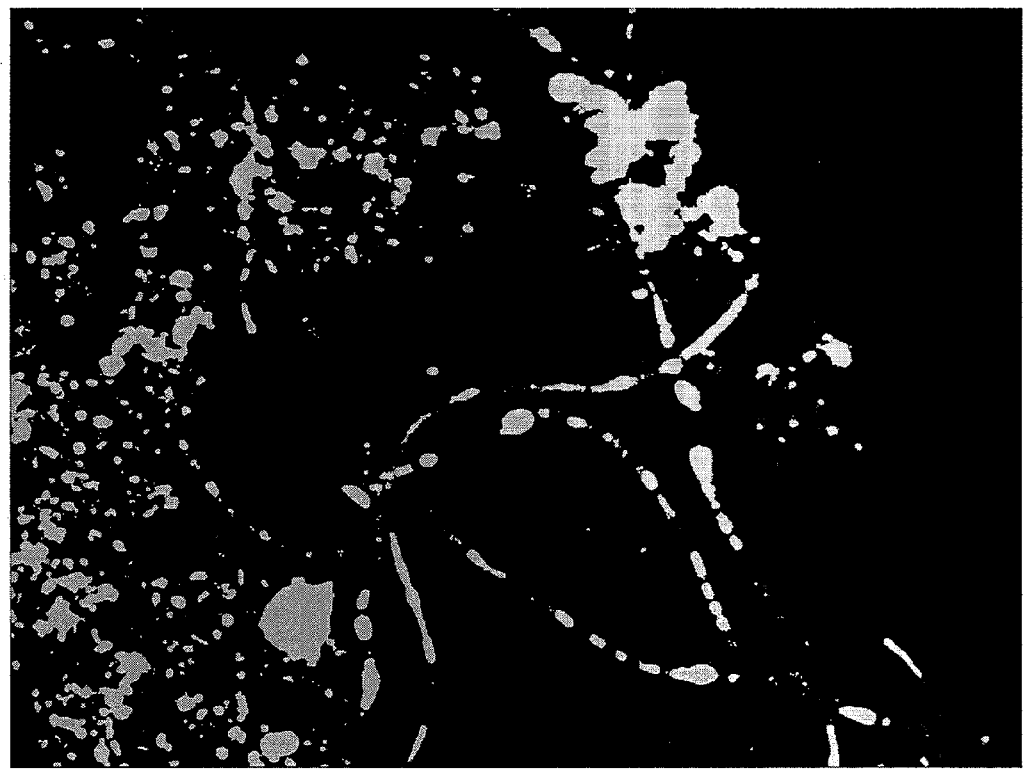
FIG. 3 is a CFDA binarized image of the same sample used in FIG. 1.
Figure 4:
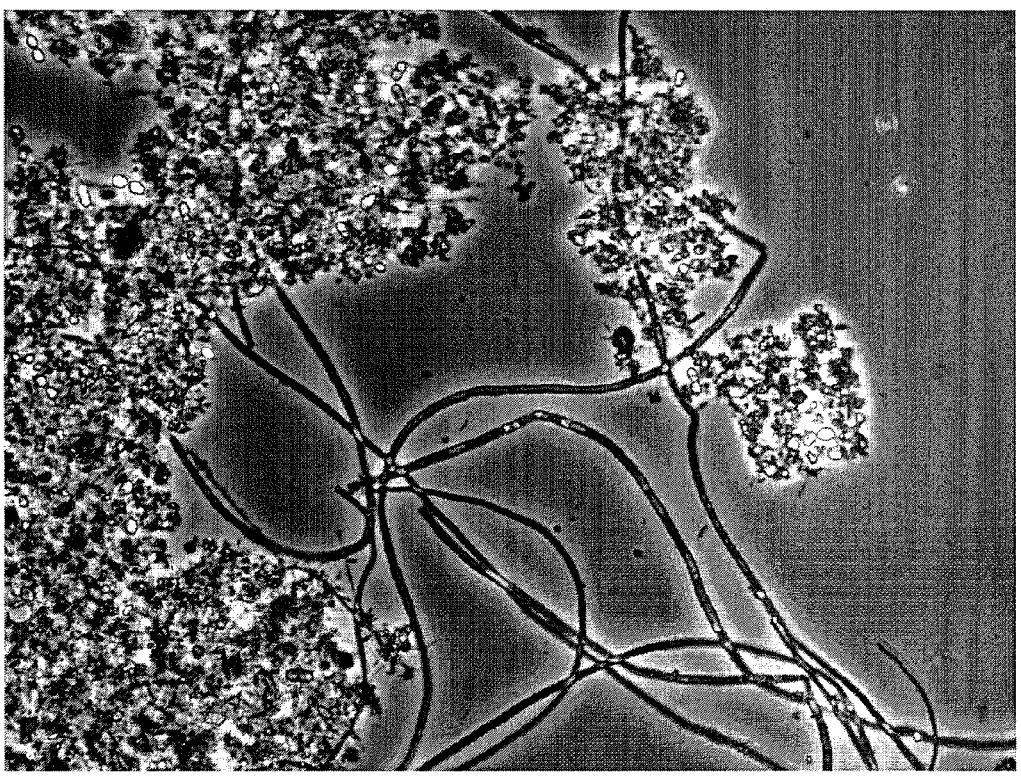
FIG. 4 is a CFDA bright field image of the same sample used in FIG. 1.
Figure 5:
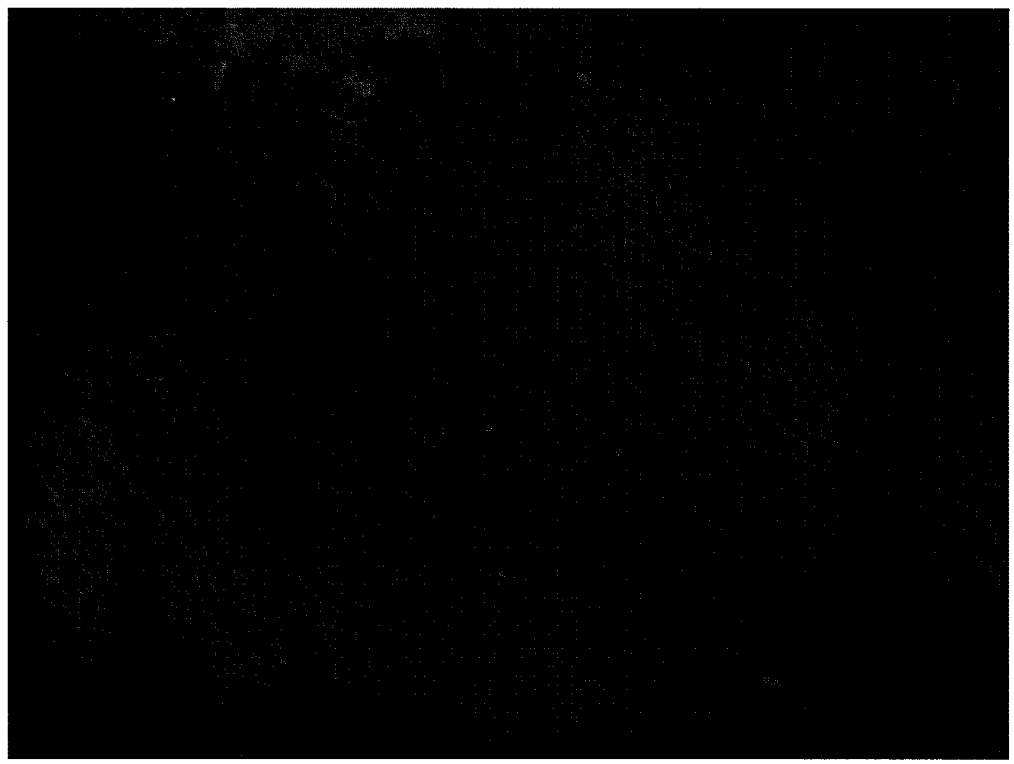
FIG. 5 is a PI fluorescent image of the same sample used in FIG. 1.
Figure 6:
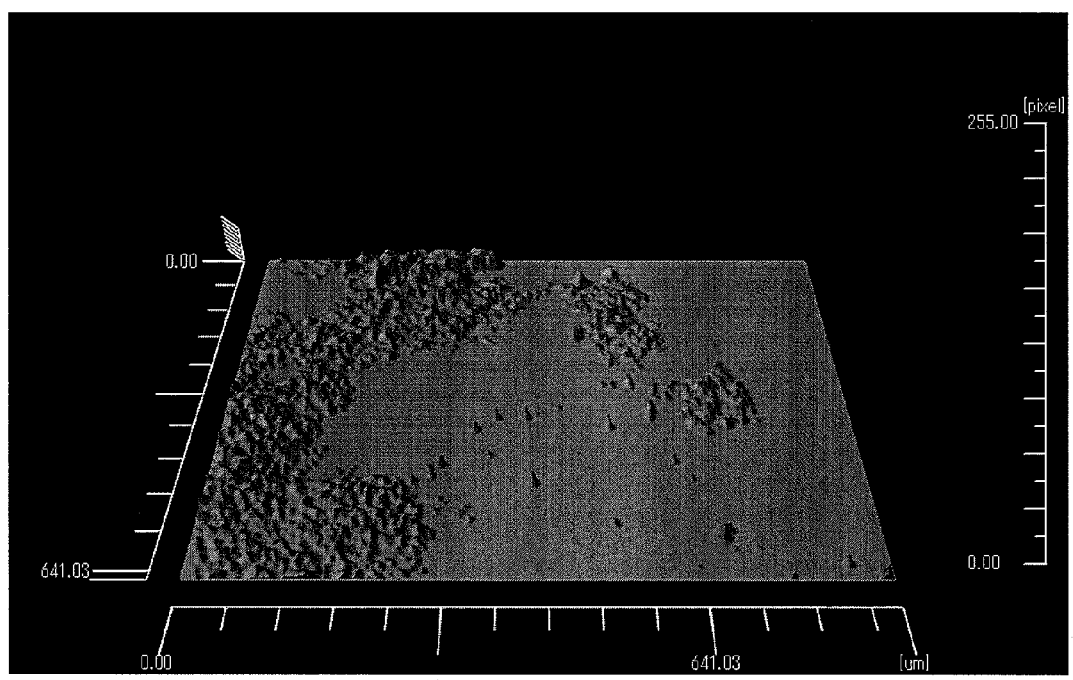
FIG. 6 is an image for the measurement of the total amount of PI fluorescence of the same sample used in FIG. 1.
Figure 7:
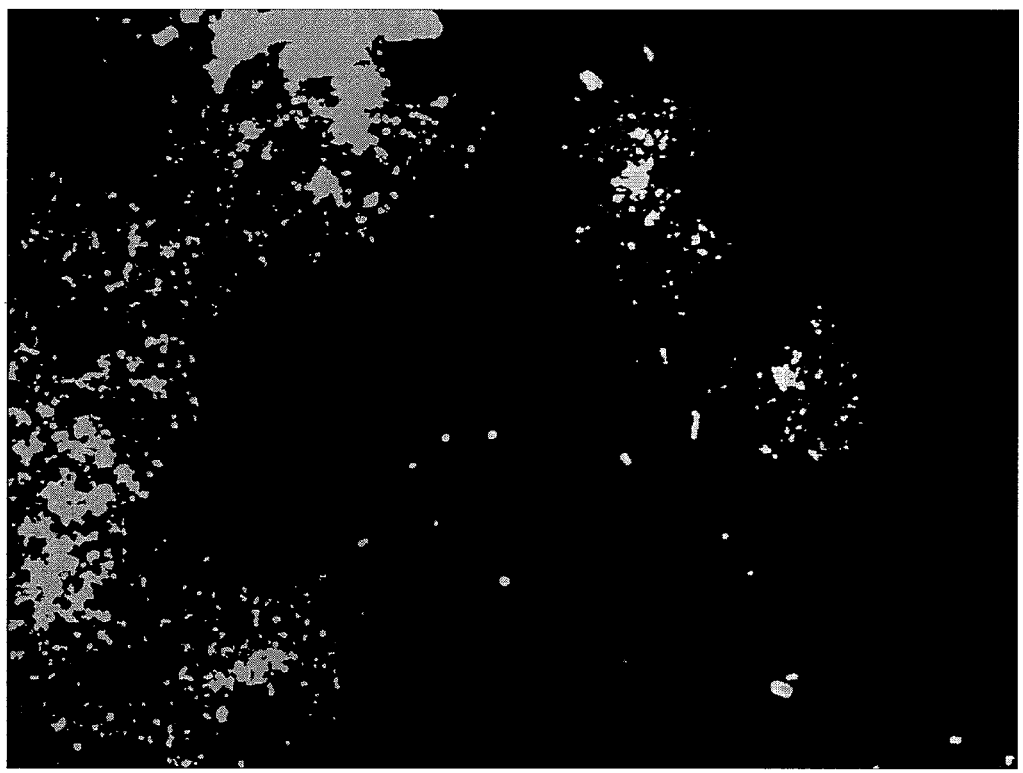
FIG. 7 is a PI binarized image of the same sample used in FIG. 1.

FIG. 1 to FIG. 7 are fluorescent staining images of PI and CFDA of samples in which sludge flocks before initiation of a test (before the addition) are subjected to double staining. FIG. 1 is a CFDA fluorescent image of a sample before the addition of a microbial preparation, FIG. 2 is an image for the measurement of the total amount of CFDA fluorescence of the same sample used in FIG. 1, FIG. 3 is a CFDA binarized image of the same sample used in FIG. 1, FIG. 4 is a CFDA bright field image of the same sample used in FIG. 1, FIG. 5 is a PI fluorescent image of the same sample used in FIG. 1, FIG. 6 is an image for the measurement of the total amount of PI fluorescence of the same sample used in FIG. 1, and FIG. 7 is a PI binarized image of the same sample used in FIG. 1.

Each signal area was digitalized based on the above technique. As a result, the obtained value of a ratio PI signal area/CFDA signal area was 0.66.

In the microbial community constituting the activated sludge, a cell population to be stained with PI is a nonproliferating cell and tends to contribute to an improvement in cohesiveness of the activated sludge, while a cell population to be stained with CFDA is often bacterium in a dispersion proliferation state that can cause bulking, or a filamentous bacterium during proliferation. In the case of the samples before the addition of a microbial preparation shown in FIG. 1 to FIG. 7, a lot of CFDA signals derived from filamentous bacteria during proliferation are recognized and PI signal area/CFDA area is 0.66 and is lower than 1.0 set as an indicator of bulking. As a result, it was determined as a state where an improvement in the physiological state of the microbial community constituting the activated sludge is required.

[Improvement of Cohesiveness of Sludge-Constituting Microbial Community by the Addition of Microbial Preparation]

In the above activated sludge treatment facility, microbial preparation (SEIKO PMC CORPORATION under the trade name of MC-008) was added to an aeration tank for 8 days for the purpose of improving the physiological state of the activated sludge. The amount of the microbial preparation charged was 11 kg/day.

Figure 8:
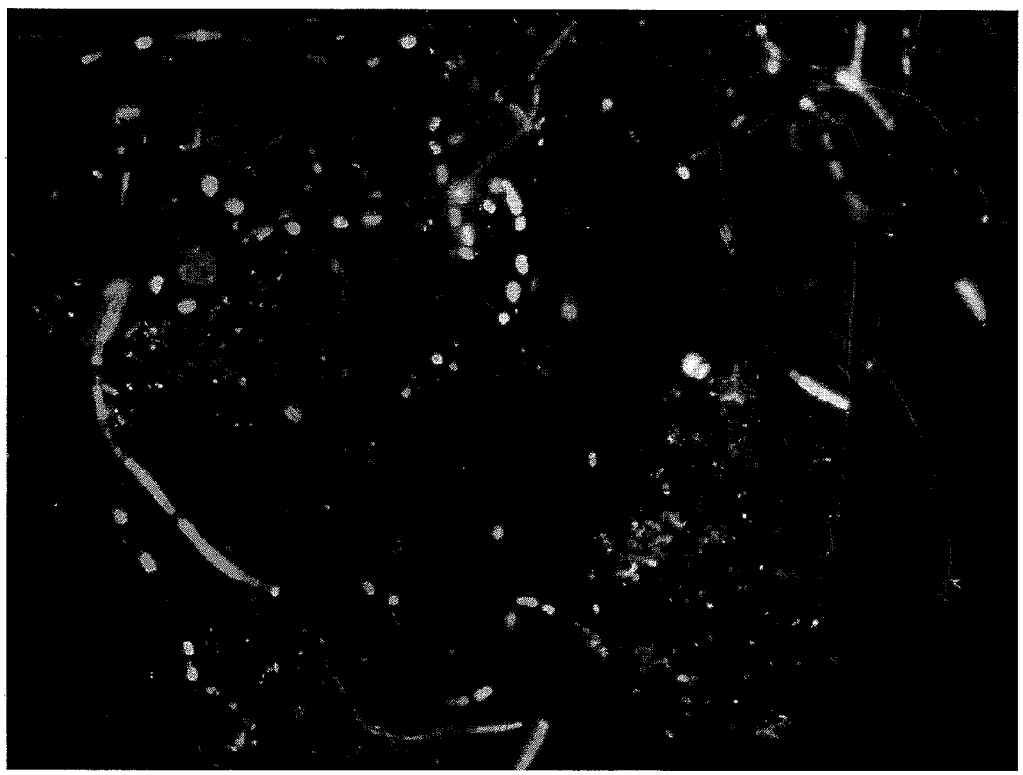
FIG. 8 is a CFDA fluorescent image of a sample on the 9th day after adding a microbial preparation in Example 1.
Figure 9:
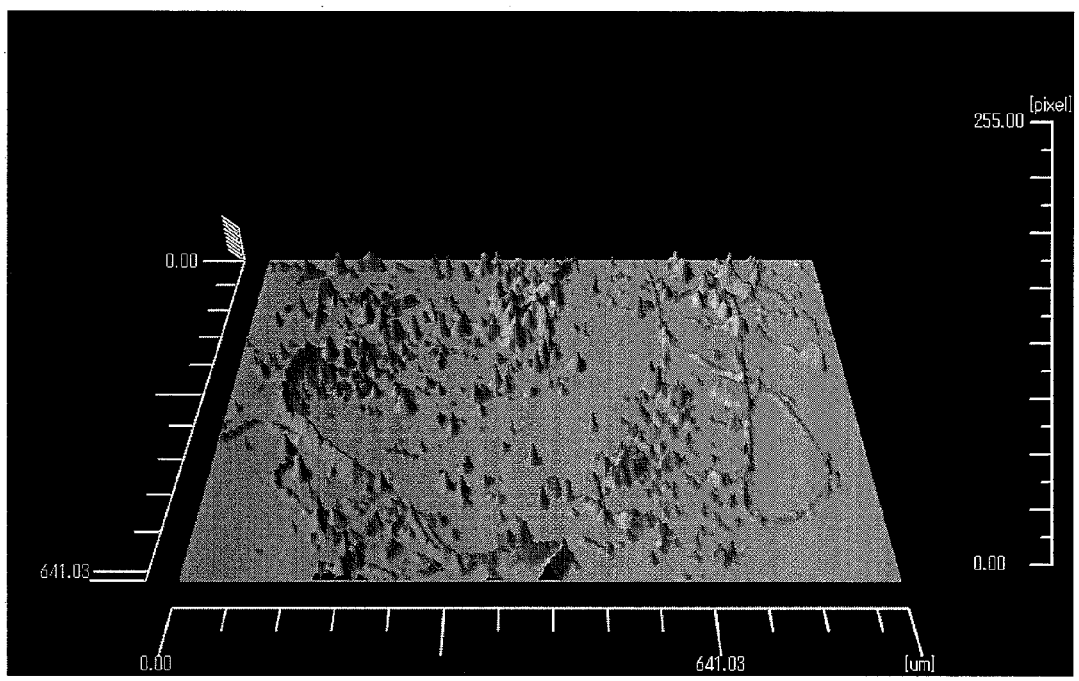
FIG. 9 is an image for the measurement of the total amount of CFDA fluorescence of the same sample used in FIG. 8.
Figure 10:
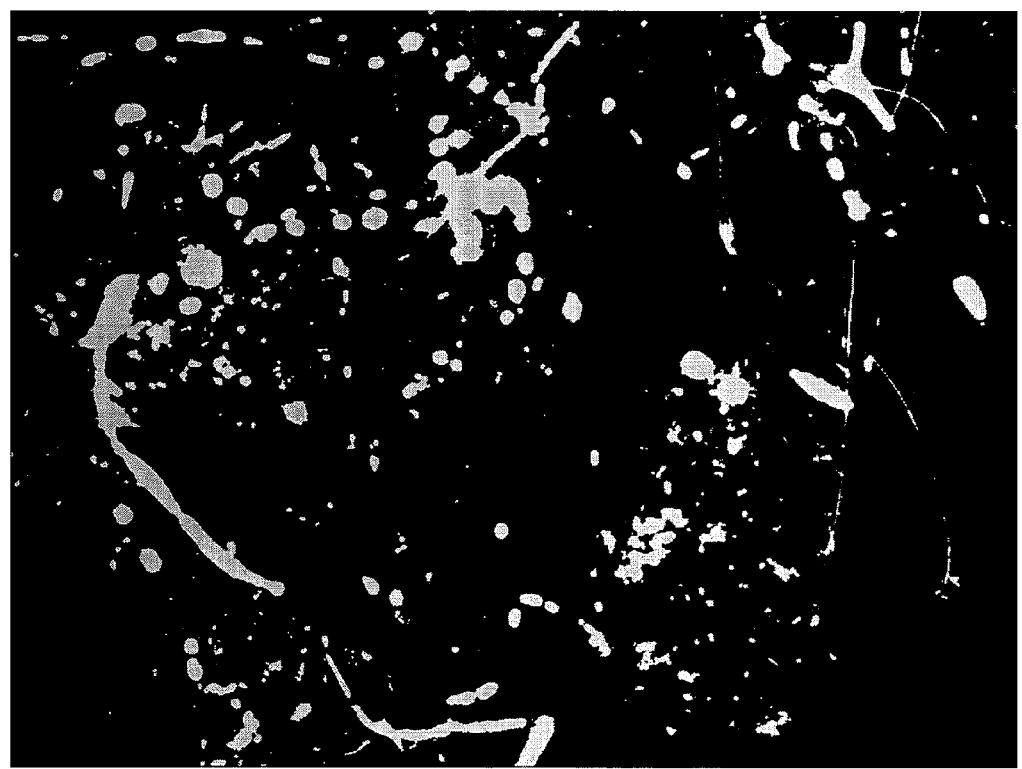
FIG. 10 is a CFDA binarized image of the same sample used in FIG. 8.
Figure 11:
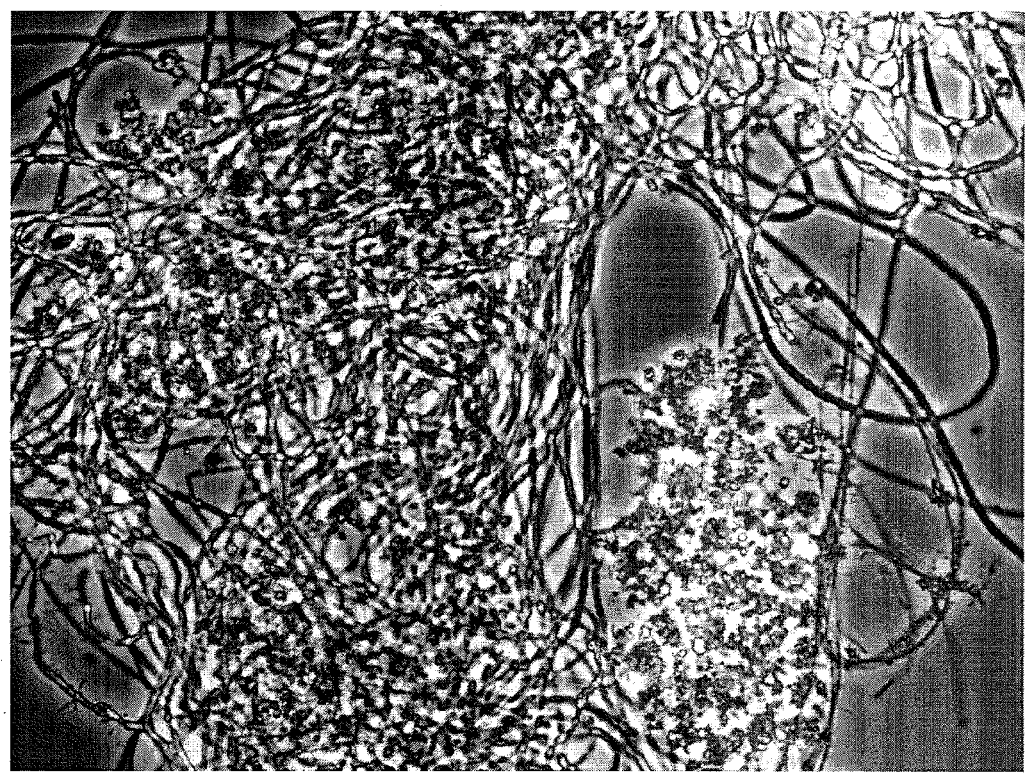
FIG. 11 is a CFDA bright field image of the same sample used in FIG. 8.
Figure 12:
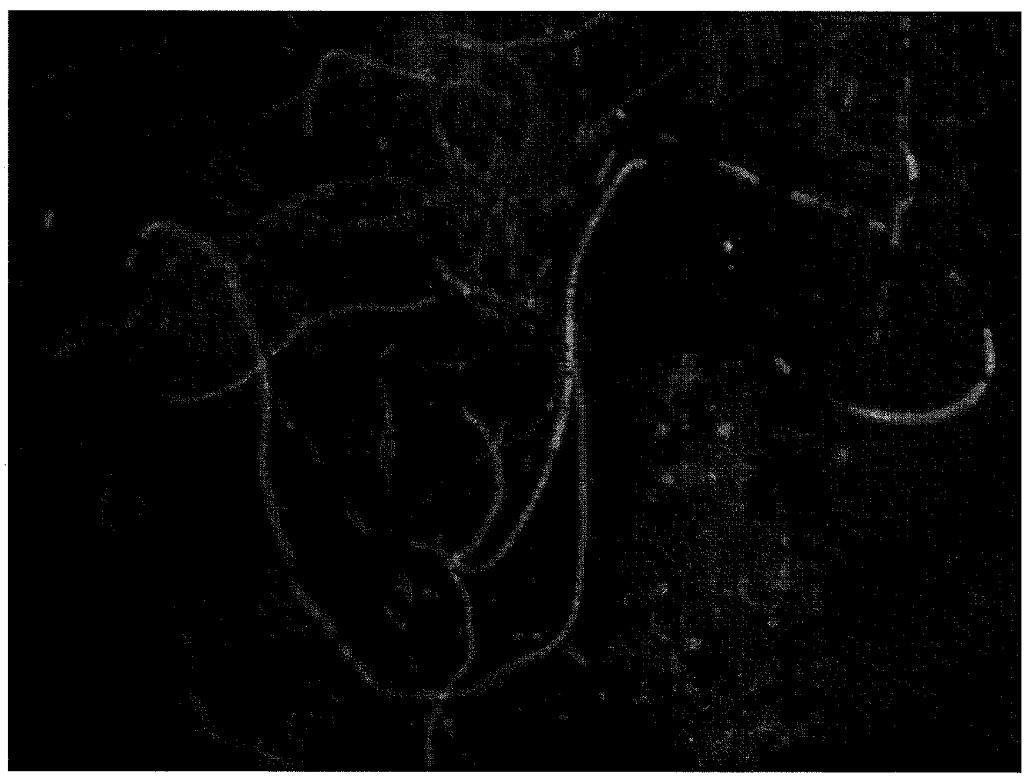
FIG. 12 is a PI fluorescent image of the same sample used in FIG. 8.
Figure 13:
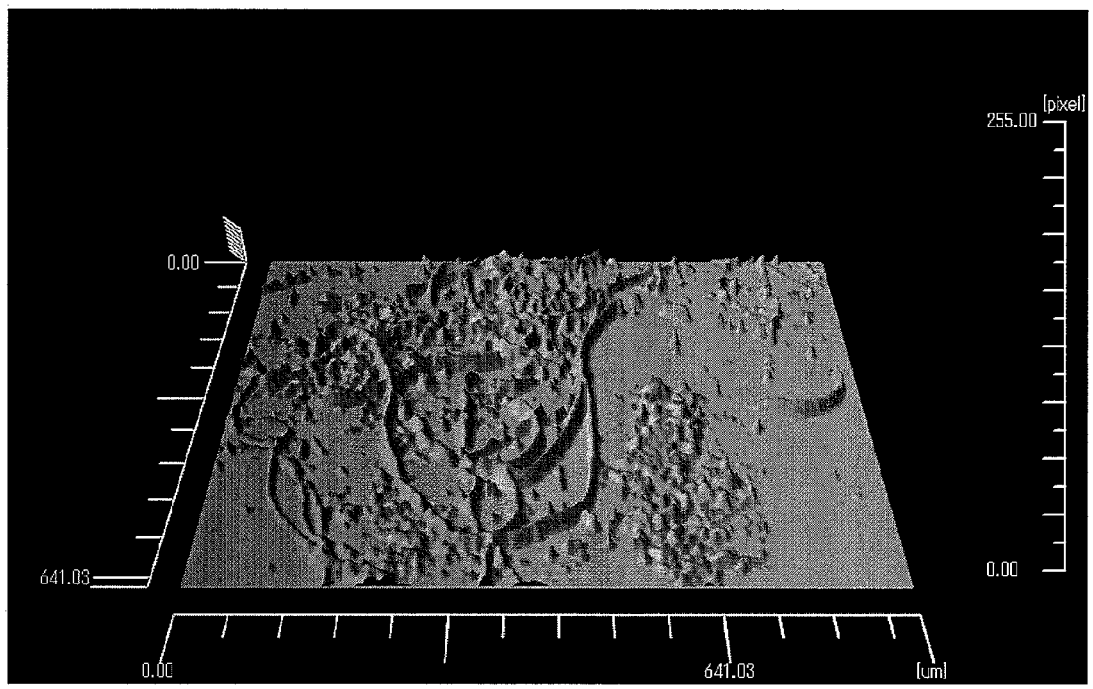
FIG. 13 is an image for the measurement of the total amount of PI fluorescence of the same sample used in FIG. 8.
Figure 14:
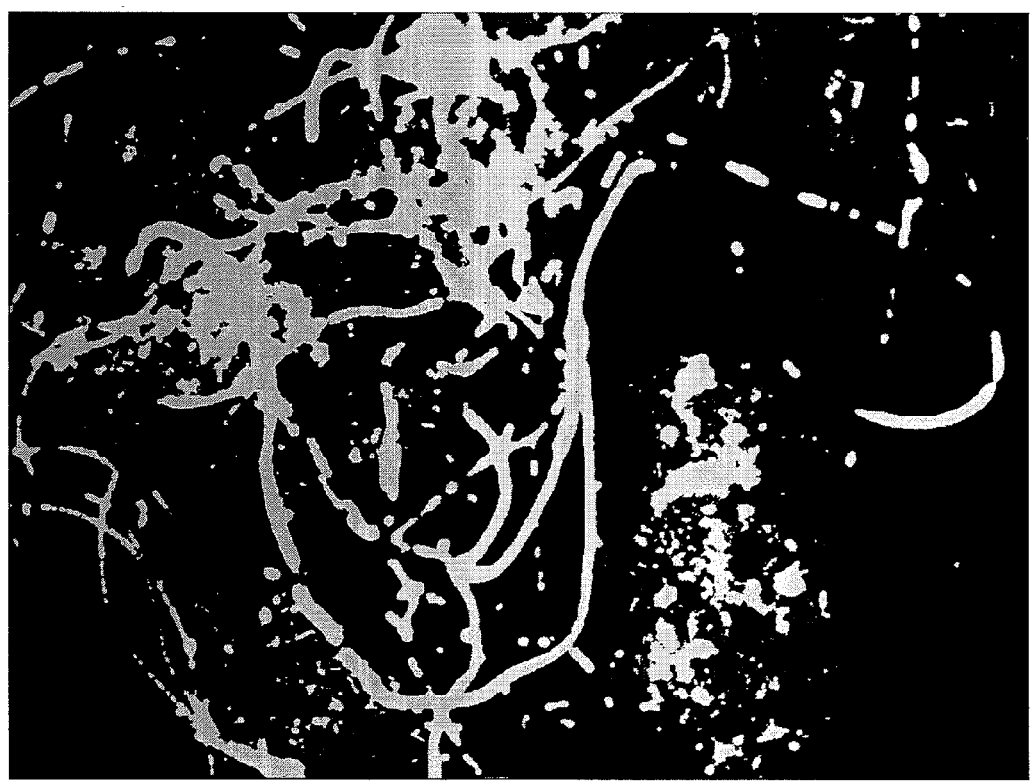
FIG. 14 is a PI binarized image of the same sample used in FIG. 8.

In Table 1, digitized data of a fluorescent staining image of the activated sludge collected during a test period and an operation parameter of a treatment tank in Example 1 are shown. FIG. 8 is a CFDA fluorescent image of a sample on the 9th day after the addition of a microbial preparation in Example 1, FIG. 9 is am image for the measurement of the total amount of CFDA fluorescence of the same sample used in FIG. 8, FIG. 10 is a CFDA binarized image of the same sample used in FIG. 8, FIG. 11 is a CFDA bright field image of the same sample used in FIG. 8, FIG. 12 is a PI fluorescent image of the same sample used in FIG. 8, FIG. 13 is an image for the measurement of the total amount of PI fluorescence of the same sample used in FIG. 8, and FIG. 14 is a PI binarized image of the same sample used in FIG. 8.

As is apparent from Table 1, although the value of the ratio PI signal area/CFDA signal area was 0.66 (that tends to cause bulking) before the addition of the microbial preparation, the value of the ratio PI signal area/CFDA signal area of the sample subjected to double staining became 2.26 which is more than the target value of 1.0 on the 9th day after the addition of the microbial preparation, and thus a large change in the physiological state of the sludge-constituting microbial community occurs. Also, the SVI value decreased by 163 ml/g compared with the case before the addition on the 9th day after the addition, and thus bulking of the sludge was improved.

Example 2

Improvement Example by Shortening Operation of Solids Retention Time in Activated Sludge System In the activated sludge treatment facility of industrial wastewater, for the purpose of improving transparency of treated water, a shortening operation of a solids retention time was conducted based on an image of fluorescent microscopy observation of the sludge-constituting microbial community.

The volume load of the target activated sludge treatment facility in the present Example is 1.2 kg-BOD/m$^3$/day.

The double staining method and the observation method of the activated sludge sample, and criterion of the physiological state of a sample were conducted in the same manner as in Example 1.

[Improvement of Cohesiveness of Sludge-Constituting Microbial Community by Shortening Operation of Solids Retention Time]

With respect to a solids retention time of an activated sludge sample before a shortening operation, a fluorescent microscopy observation was performed.

Figure 15:
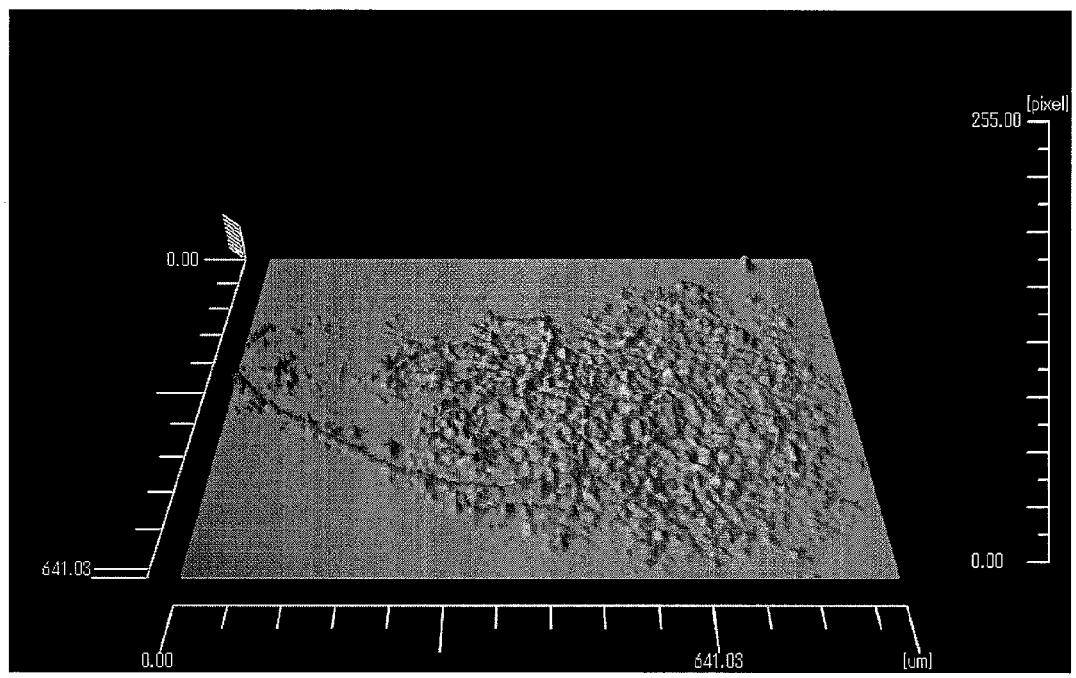
FIG. 15 is an image for the measurement of the total amount of CFDA fluorescence of a sample before a shortening treatment of a solids retention time in Example 2.
Figure 16:
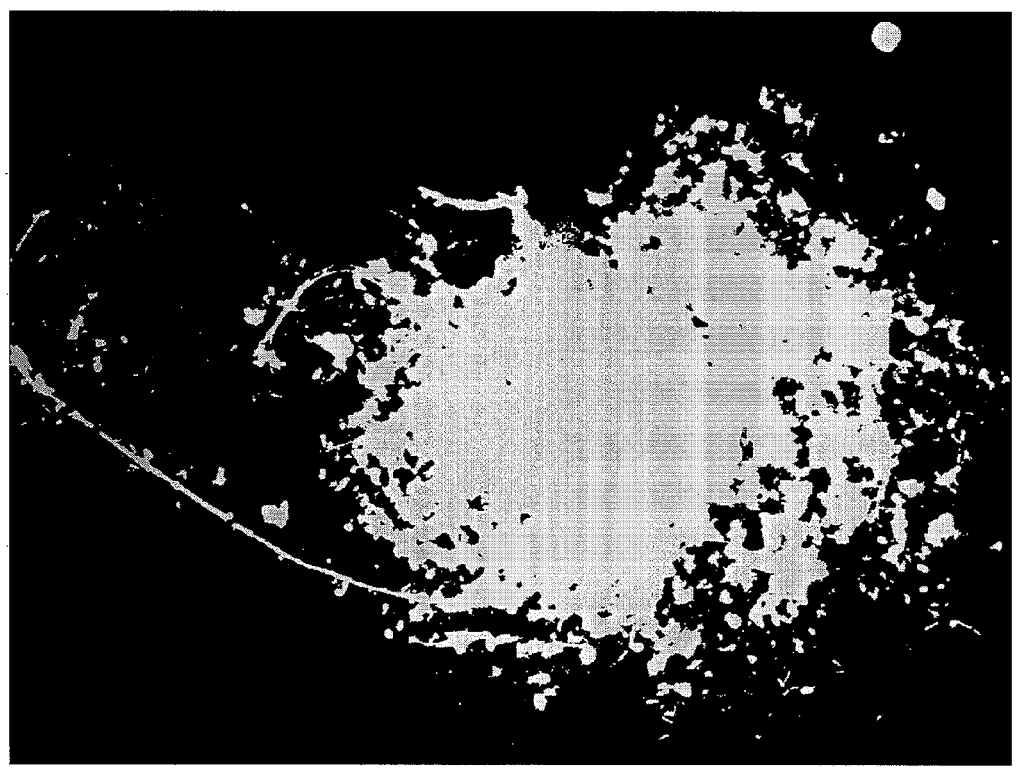
FIG. 16 is a CFDA binarized image of the same sample used in FIG. 15.
Figure 17:
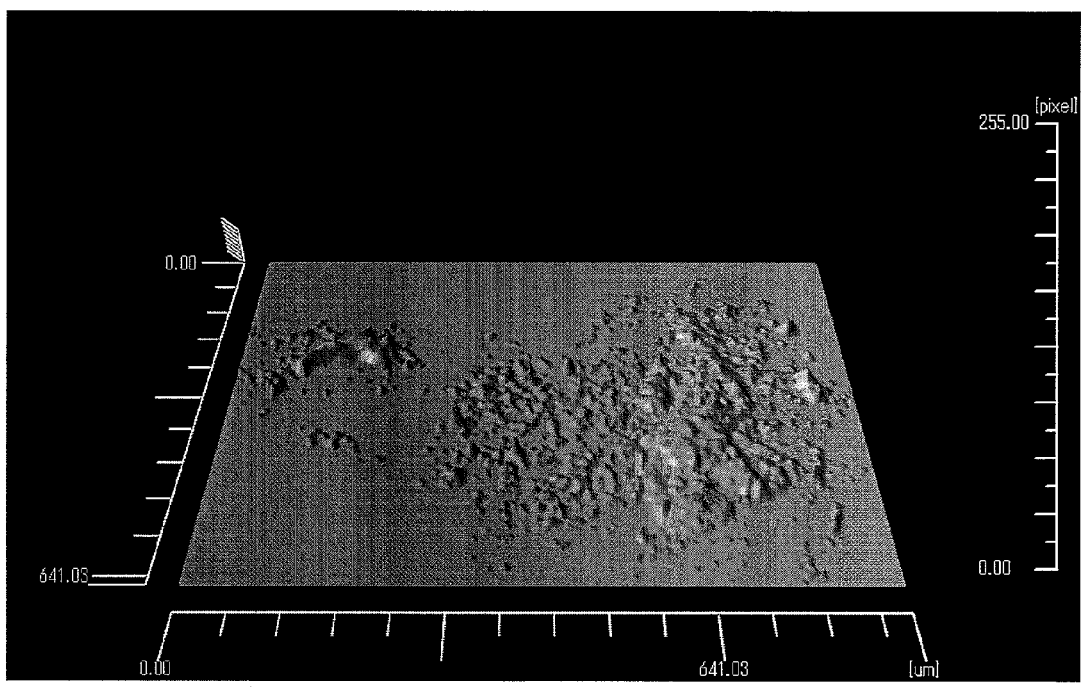
FIG. 17 is an image for the measurement of the total amount of PI fluorescence of the same sample used in FIG. 15.
Figure 18:
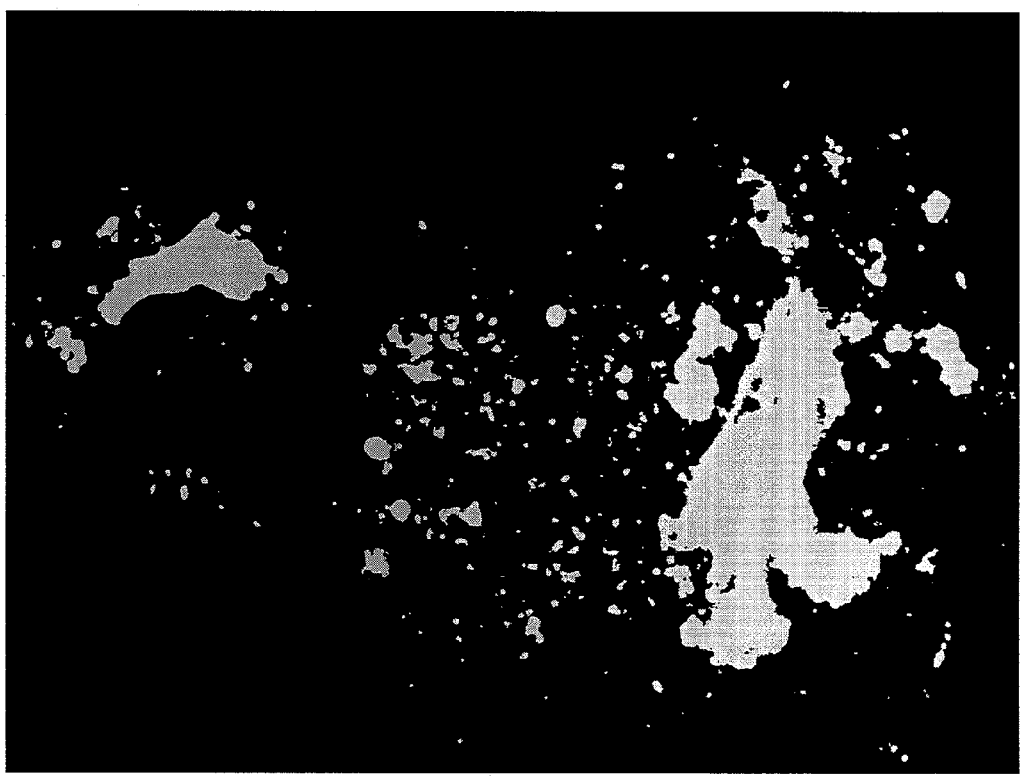
FIG. 18 is a PI binarized image of the same sample used in FIG. 15.

The results are shown in FIG. 15 to FIG. 18. FIG. 15 is an image for the measurement of the total amount of CFDA fluorescence of a sample before a shortening treatment of a solids retention time in Example 2, FIG. 16 is a CFDA binarized image of the same sample used in FIG. 15, FIG. 17 is an image for the measurement of the total amount of PI fluorescence of the same sample used in FIG. 15, and FIG. 18 is a PI binarized image of the same sample used in FIG. 15.

TABLE 1

| Situation of addition of microbial preparation | CFDA | PI | PI/CFDA | Solids retention time (days) | COD reduction rate improved value (%) | SVI improved value (ml/g) | Additive amount of MC0008 (Kg) |
| --- | --- | --- | --- | --- | --- | --- | --- |
| | | | Signal area (pixel) | | | | |
| Before addition | 51644 | 33983 | 0.66 | 3.3 | | | |
| On 9th day after addition | 45663 | 103321 | 2.26 | 3.5 | +6 | −163 | 11 |
| | | | Total fluorescence amount (pixel × luminance) | | | | |
| Before addition | 9873012 | 5156783 | 0.52 | 3.3 | | | |
| On 9th day after addition | 8819245 | 17953371 | 2.04 | 3.5 | +6 | −163 | 11 |

Concerning this sample, a PI signal area and a CFDA signal area were digitalized. In this sample, the value of a ratio PI signal area/CFDA signal area became 0.37, and it was determined that an improvement is required. In this activated sludge sample, since filamentous bacteria that can mainly cause bulking have high proliferation properties and tend to be strongly stained with CFDA, a trial of improving proliferation properties due to a shortening operation of a solids retention time was made by increasing draw of the sludge.

[Improvement by Shortening Operation of Solids Retention Time]

In this activated sludge treatment facility, an operation of shortening the solids retention time from 12.6 days to 6.7 days was performed. On the 35th day after the initiation of the treatment, a fluorescent microscopy observation of the sludge was performed again.

Figure 19:
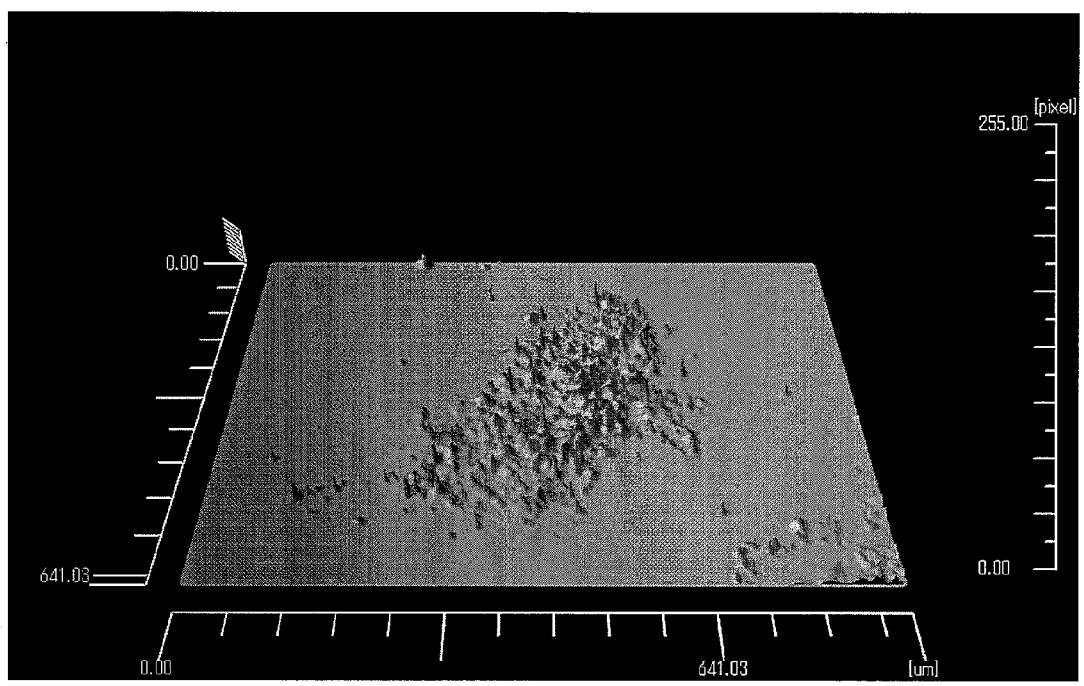
FIG. 19 is an image for the measurement of the total amount of CFDA fluorescence of a sample after a shortening treatment of a solids retention time in Example 2.
Figure 20:
FIG. 20 is a CFDA binarized image of the same sample used in FIG. 19.
Figure 21:
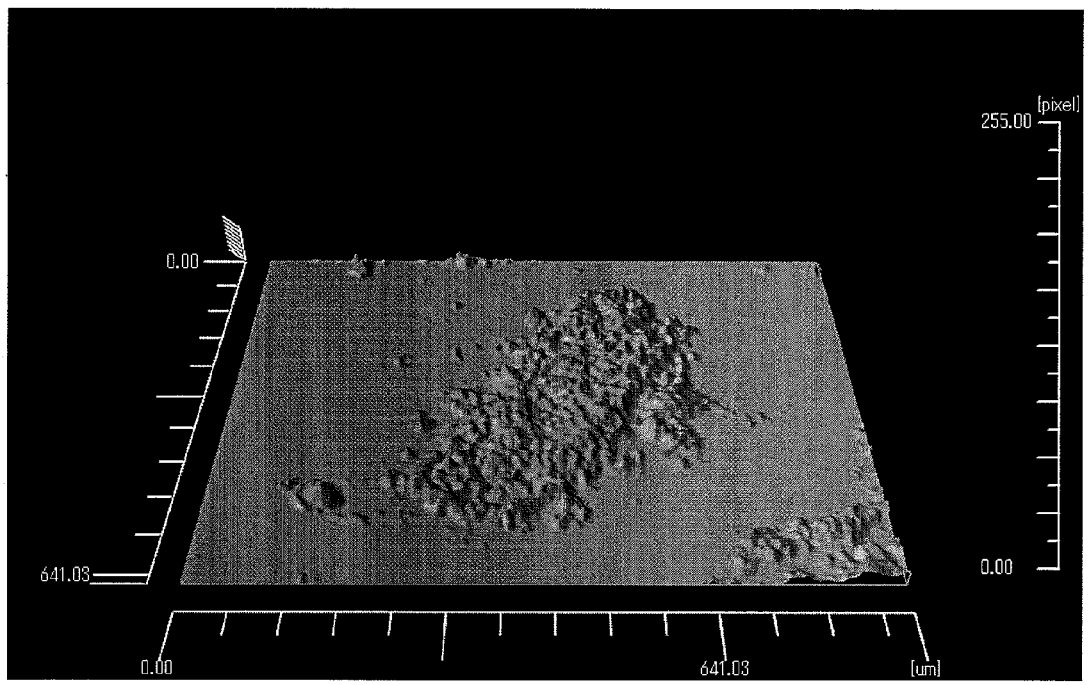
FIG. 21 is an image for the measurement of the total amount of PI fluorescence of the same sample used in FIG. 19.
Figure 22:
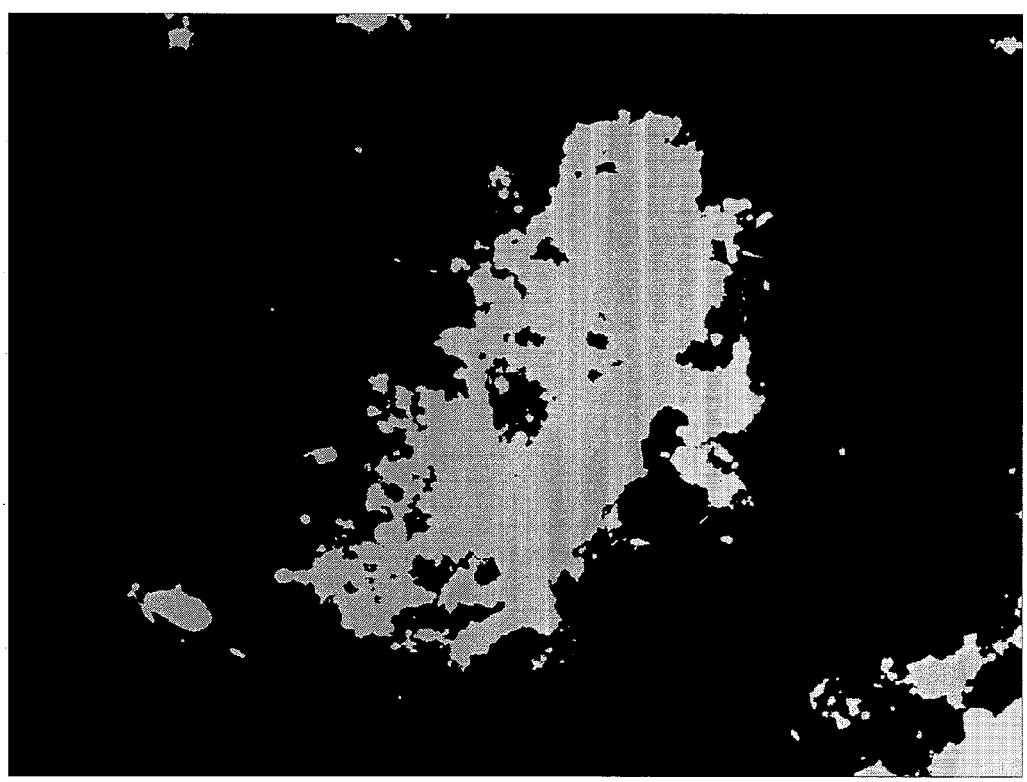
FIG. 22 is a PI binarized image of the same sample used in FIG. 15.

In Table 2, digitized data of a fluorescent staining image of the activated sludge collected during a test period and an operation parameter of a treatment tank in Example 2 are shown. FIG. 19 is an image for the measurement of the total amount of CFDA fluorescence of a sample after a shortening treatment of solids retention time in Example 2, FIG. 20 is CFDA binarized image of the same sample used in FIG. 19, FIG. 21 is an image for the measurement of the total amount of PI fluorescence of the same sample used in FIG. 19, and FIG. 22 is a PI binarized image of the same sample used in FIG. 19.

and improving a COD reduction rate, the addition of a microbial preparation and a shortening operation of a solids retention time were performed based on an image of fluorescent microscopy observation of a sludge-constituting microbial community.

The volume load of the target activated sludge treatment facility in the present Example is 2.2 kg-BOD/m$^3$/day.

The double staining method and the observation method of the activated sludge sample, and criterion of the physiological state of a sample were conducted in the same manner as in Example 1.

[Improvement by the Addition of Microbial Preparation to Activated Sludge System and Operation of Shortening Solids Retention Time]

Figure 23:
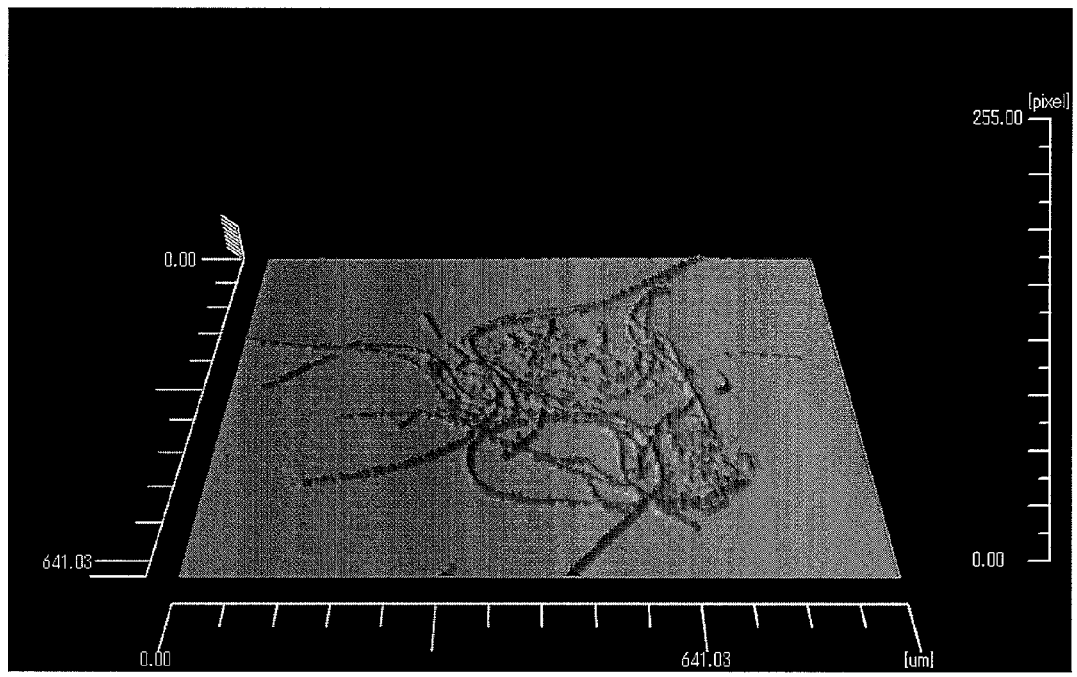
FIG. 23 is an image for the measurement of the total amount of CFDA fluorescence of a sample before the addition of a microbial preparation and a shortening treatment of a solids retention time in Example 3.
Figure 24:
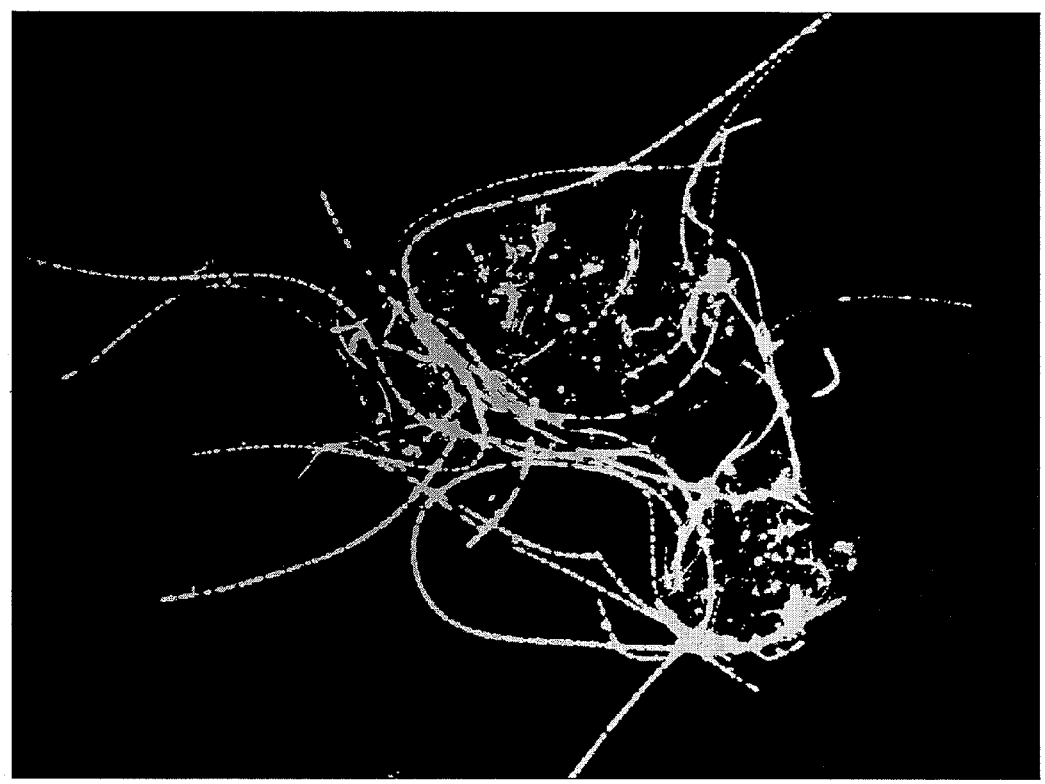
FIG. 24 is a CFDA binarized image of the same sample used in FIG. 23.
Figure 25:
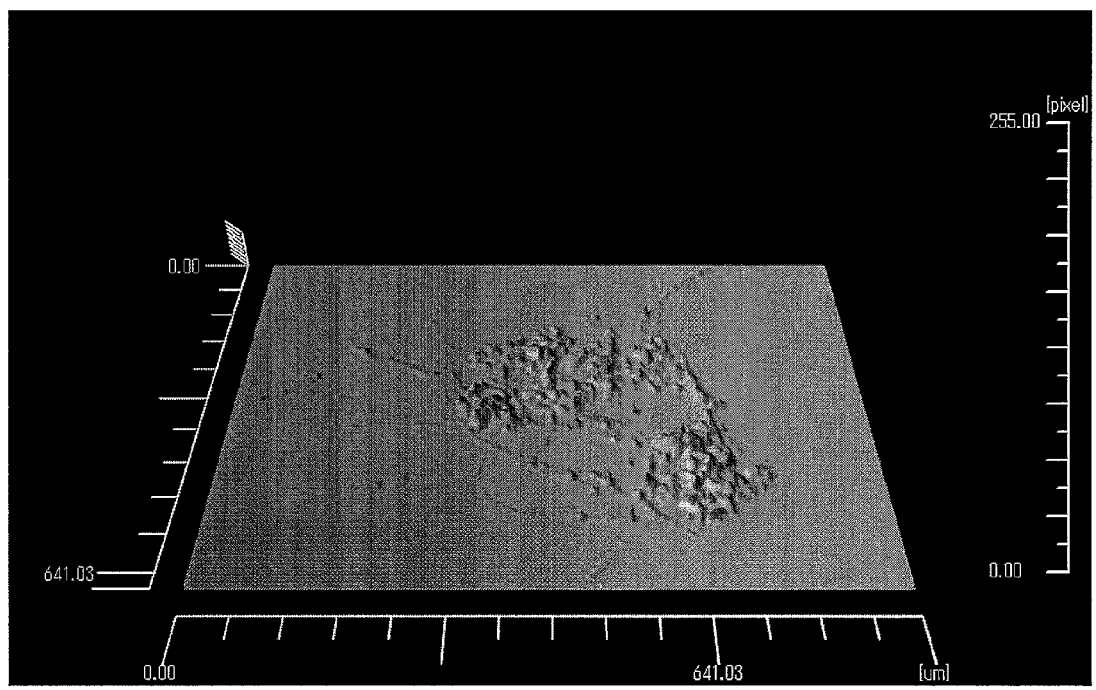
FIG. 25 is an image for the measurement of the total amount of PI fluorescence of the same sample used in FIG. 23.
Figure 26:
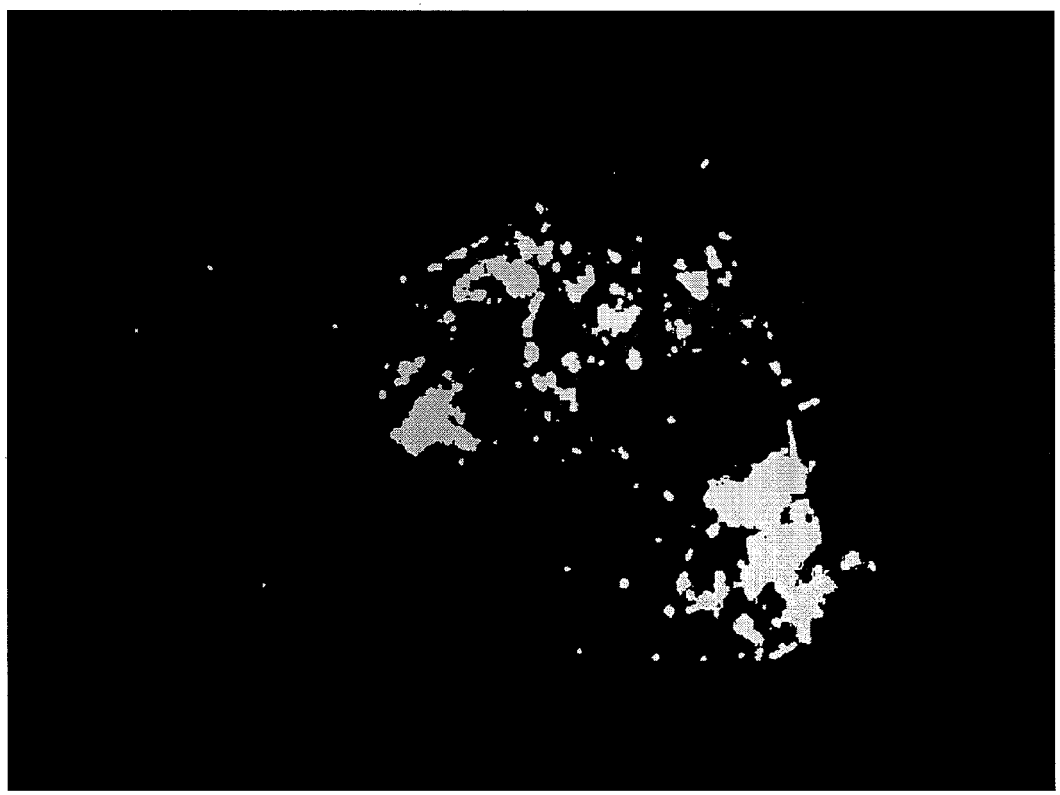
FIG. 26 is a PI binarized image of the same sample used in FIG. 23.

Concerning an activated sludge sample before the operation, fluorescent microscopy observation was performed. The results are shown in FIG. 23 to FIG. 26. FIG. 23 is an image for the measurement of the total amount of CFDA fluorescence of a sample before a shortening treatment of a solids retention time in Example 3, FIG. 24 is a CFDA binarized image of the same sample used in FIG. 23, FIG. 25 is an image for the measurement of the total amount of PI fluorescence of the same sample used in FIG. 23, and FIG. 26 is a PI binarized image of the same sample used in FIG. 23.

Concerning this sample, a PI signal area and a CFDA signal area were digitalized. In this sample, the value of a ratio PI signal area/CFDA signal area became 0.56, and it was deter-

TABLE 2

| | CFDA | PI | PI/CFDA | Solids retention time (days) | Solids retention time of formula 1 | Transparency of treated water (cm) |
|---|---|---|---|---|---|---|
| | | | Signal area (pixel) | | | |
| Before operation | 150780 | 56499 | 0.37 | 12.6 | 8.4 | 20 |
| On 35th day after operation | 34069 | 93388 | 2.74 | 6.7 | 5.2 | 30 |
| | | | Total fluorescence amount (pixel × luminance) | | | |
| Before operation | 16709734 | 6105772 | 0.37 | 12.6 | 8.4 | 20 |
| On 35th day after operation | 4448757 | 12212256 | 2.75 | 6.7 | 5.2 | 30 |

As is apparent from Table 2, although the value of the ratio PI signal area/CFDA signal area was 0.37 (that tends to cause bulking) before the shortening operation of the solids retention time, the operation of shortening the solids retention time from 12.6 days to 6.7 days and the value of the ratio PI signal area/CFDA signal area became 2.74 on the 35th day after the initiation of the treatment, and thus a change in the physiological state of the sludge-constituting microbial community was recognized. By mainly suppressing proliferation of filamentous bacteria that emitted fluorescence by CFDA staining, cohesiveness of the sludge was improved and thus the target transparency of treated water was remarkably improved from 20 cm to 30 cm.

Example 3

Improvement Example by the Addition of Microbial Preparation to Activated Sludge System and Operation of Shortening Solids Retention Time In an activated sludge treatment facility of industrial wastewater, for the purpose of improving settleability of a sludge mined that an improvement is required. In this activated sludge sample, since filamentous bacteria that can mainly cause bulking have high proliferation properties and tend to be strongly stained with CFDA, a trial of improving proliferation properties was made by the addition of a microbial preparation and a shortening operation of a solids retention time.

In this activated sludge treatment facility, a trial of an improvement was made by the addition of a microbial preparation (SEIKO PMC under the trade name of MC-008) to an aeration tank for 8 days and an operation of decreasing a solids retention time from 12.4 days to 12.0 day. The amount of the microbial preparation was 5.7 kg/day.

Figure 27:
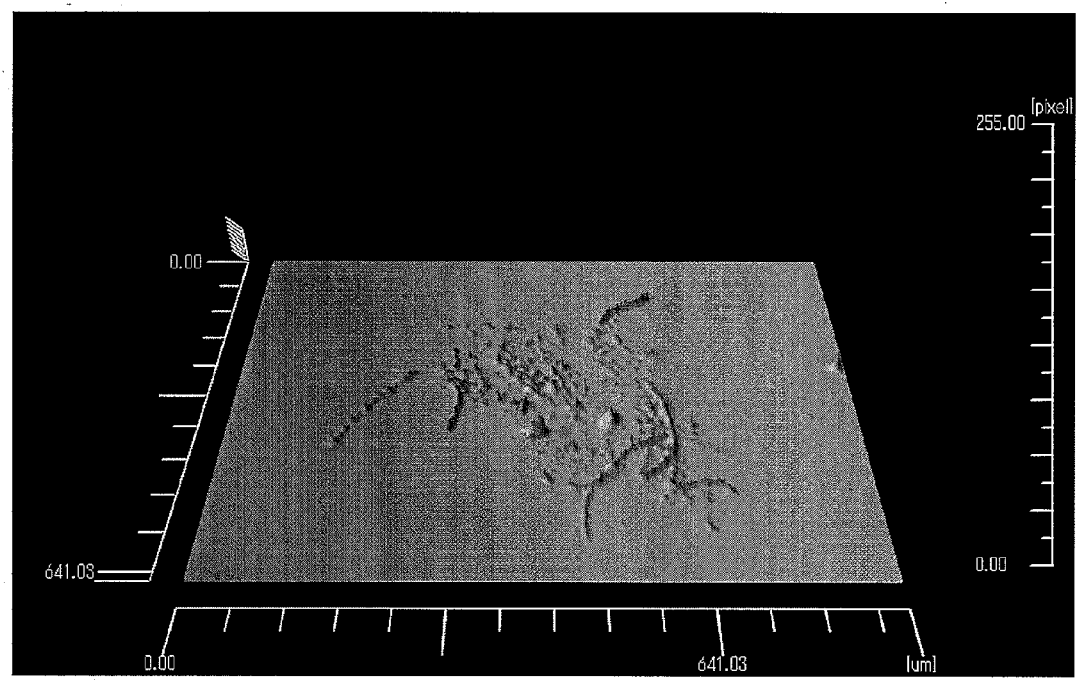
FIG. 27 is an image for the measurement of the total amount of CFDA fluorescence on the 28th day after the addition of a microbial preparation and a shortening treatment of a solids retention time in Example 3.
Figure 28:
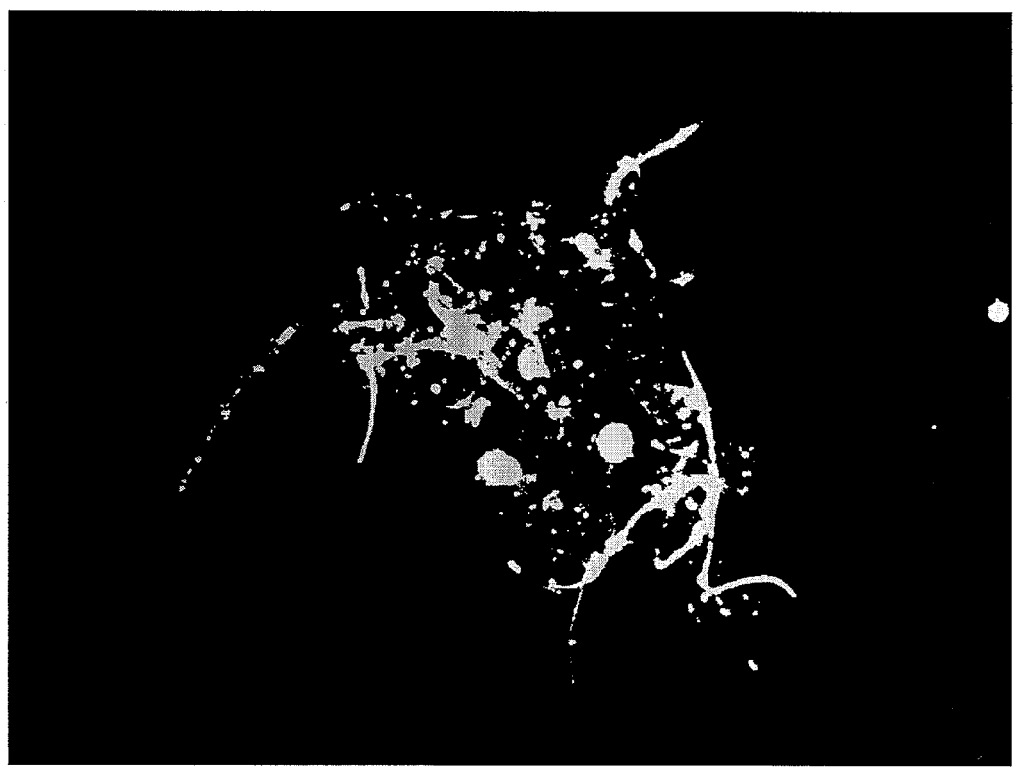
FIG. 28 is a CFDA binarized image of the same sample used in FIG. 27.
Figure 29:
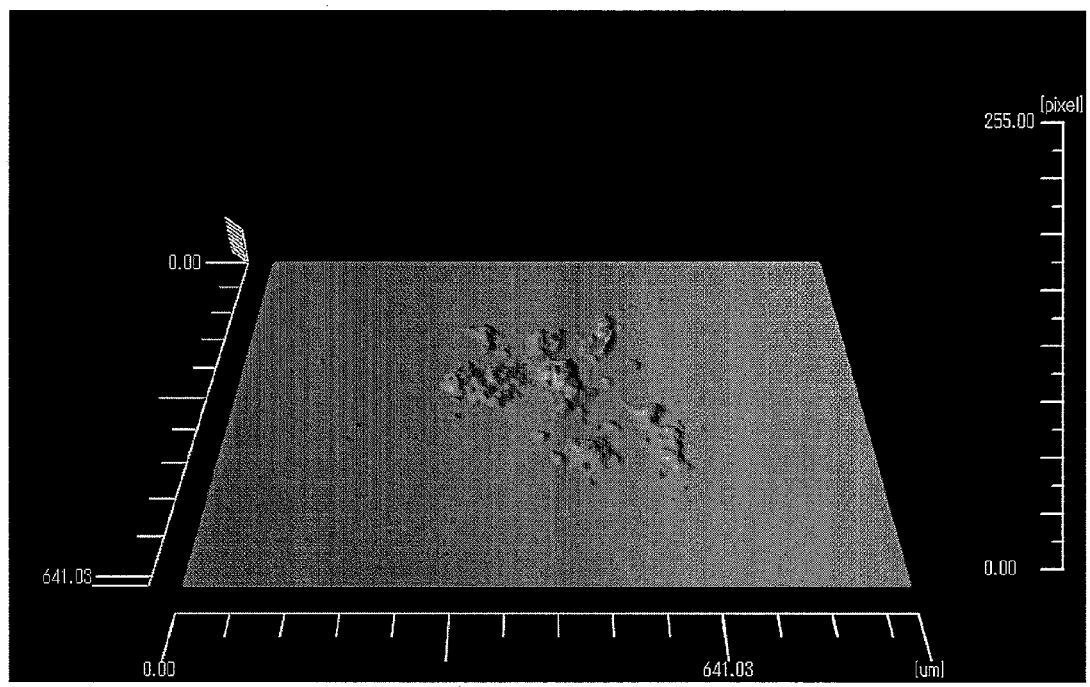
FIG. 29 is an image for the measurement of the total amount of PI fluorescence of the same sample used in FIG. 27.
Figure 30:
FIG. 30 is a PI binarized image of the same sample used in FIG. 27.

On the 28th day after the addition of the microbial preparation and the initiation of the shortening operation of the solids retention time, fluorescent microscopy observation of the sludge was performed again. FIG. 27 is an image for the measurement of the total amount of CFDA fluorescence of a sample on the 28th day after the addition of a microbial preparation and a shortening treatment of a solids retention time in Example 3, FIG. 28 is a CFDA binarized image of the same sample used in FIG. 27, FIG. 29 is an image for the measurement of the total amount of PI fluorescence of the same sample used in FIG. 27, and FIG. 30 is a PI binarized image of the same sample used in FIG. 27.

Concerning the sample after 28 days, a PI signal area and a CFDA signal area were digitalized. In this sample, the value of a ratio PI signal area/CFDA signal area became 0.92, and a tendency of an improvement was recognized in the physiological state of the sludge-constituting microbial community, and an improvement in a COD reduction rate was also recognized. However, settleability represented by SV30 as one of the targets of the sludge was not improved.

Therefore, an operation of shortening the solids retention time to 6.2 days by further increasing the draw amount of the sludge was added.

Figure 31:
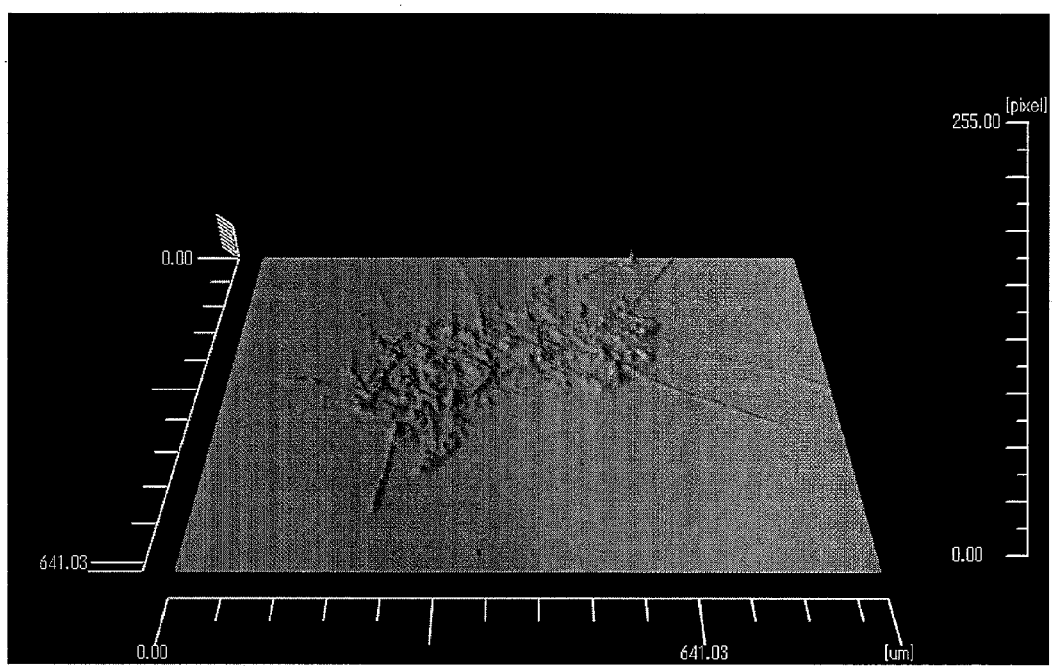
FIG. 31 is an image for the measurement of the total amount of CFDA fluorescence on the 70th day after the addition of a microbial preparation and a shortening treatment of a solids retention time in Example 3.
Figure 32:
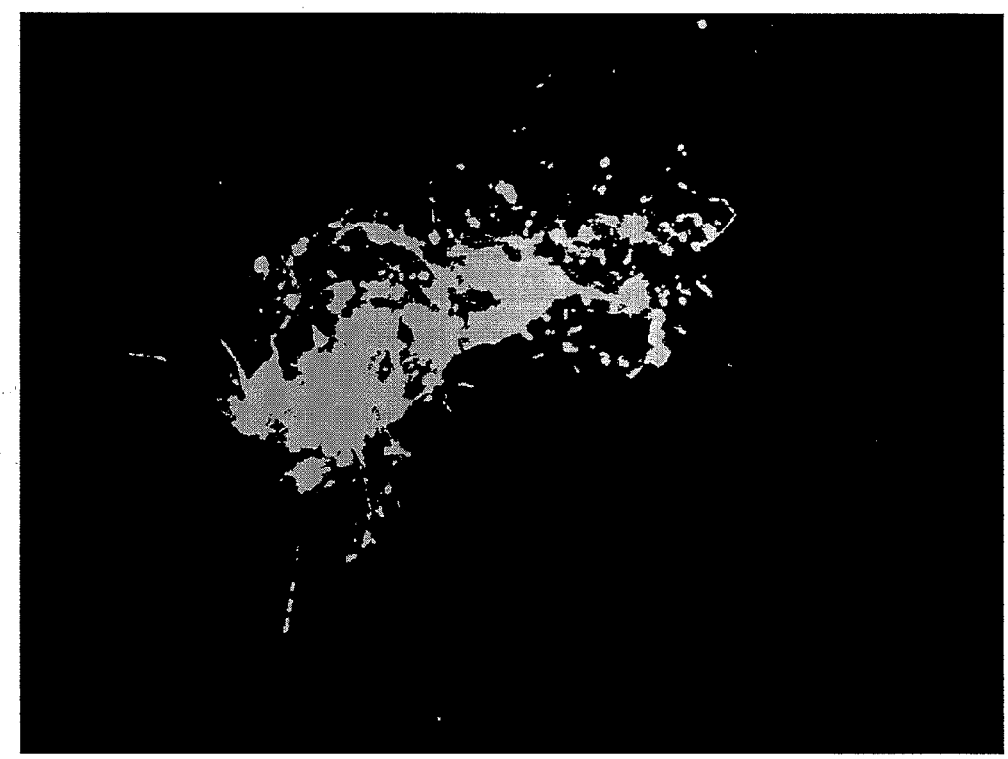
FIG. 32 is a CFDA binarized image of the same sample used in FIG. 31.
Figure 33:
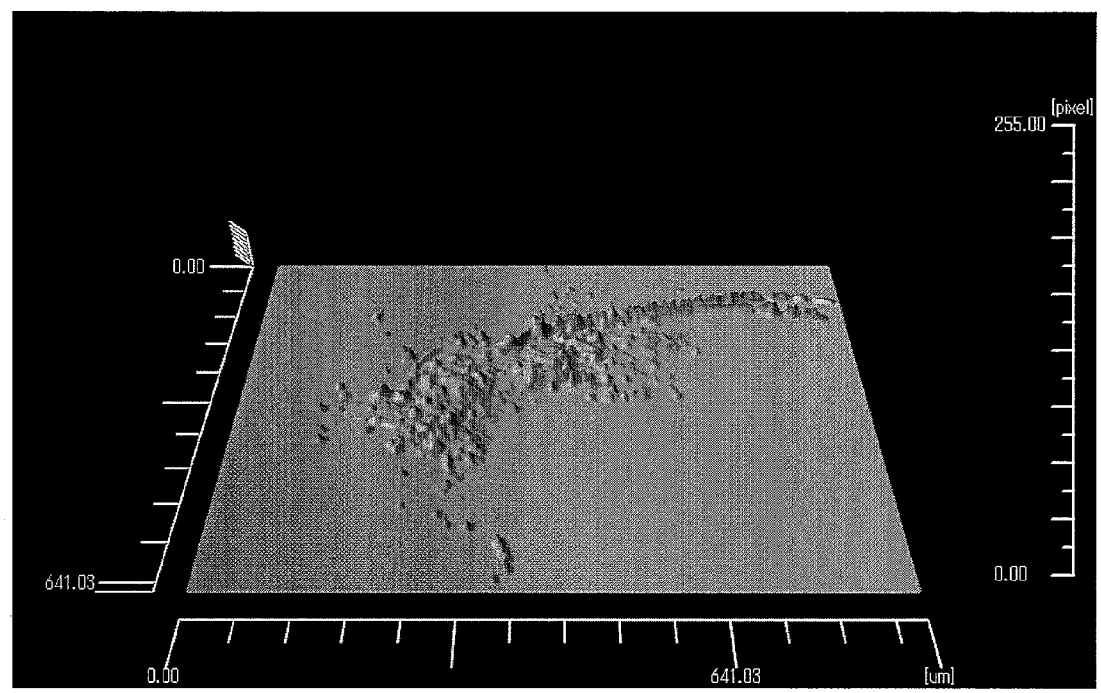
FIG. 33 is an image for the measurement of the total amount of PI fluorescence of the same sample used in FIG. 31.
Figure 34:
FIG. 34 is a PI binarized image of the same sample used in FIG. 31.

In Table 3, digitized data of a fluorescent staining image of the activated sludge collected during a test period and an operation parameter of a treatment tank in Example 3 are shown. FIG. 31 is an image for the measurement of the total amount of CFDA fluorescence of a sample on the 70th day after the addition of a microbial preparation and a shortening treatment of a solids retention time in Example 3, FIG. 32 is a CFDA binarized image of the same sample used in FIG. 31, FIG. 33 is an image for the measurement of the total amount of PI fluorescence of the same sample used in FIG. 31, and FIG. 34 is a PI binarized image of the same sample used in FIG. 31.

water, a measure was taken by the addition of a microbial preparation based on an image of fluorescent microscopy observation of a sludge constituting-microbial community. The double staining method and the observation method of the activated sludge sample, and criterion of the physiological state of a sample were conducted in the same manner as in Example 1.

The target biofilm treatment facility in the present Example is the facility in which a wastewater treatment is performed by adhering a microbe to a carrier in a treatment tank, and it is not necessary to return the carrier since the carrier usually does not flow out of the system. The volume load of the target biofilm treatment facility in the present Example is 3.0 kg-BOD/$m^3$/day.

[Improvement of COD Reduction Rate by the Addition of Microbial Preparation]

Figure 35:
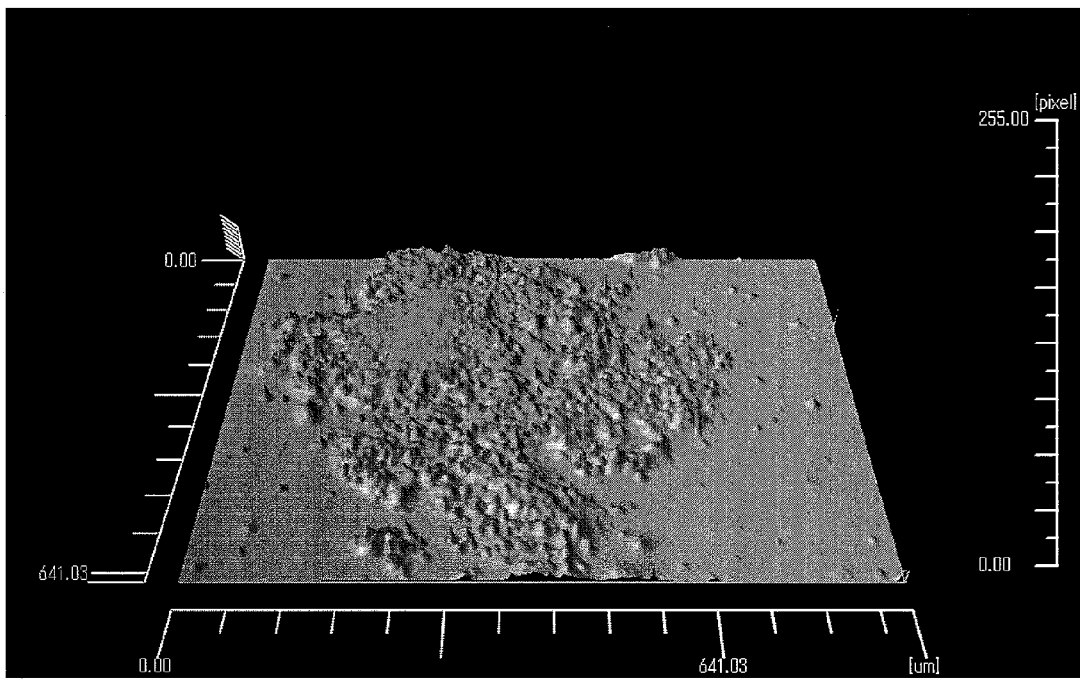
FIG. 35 is an image for the measurement of the total amount of CFDA fluorescence of a sample before the addition of a microbial preparation in Example 4.
Figure 36:
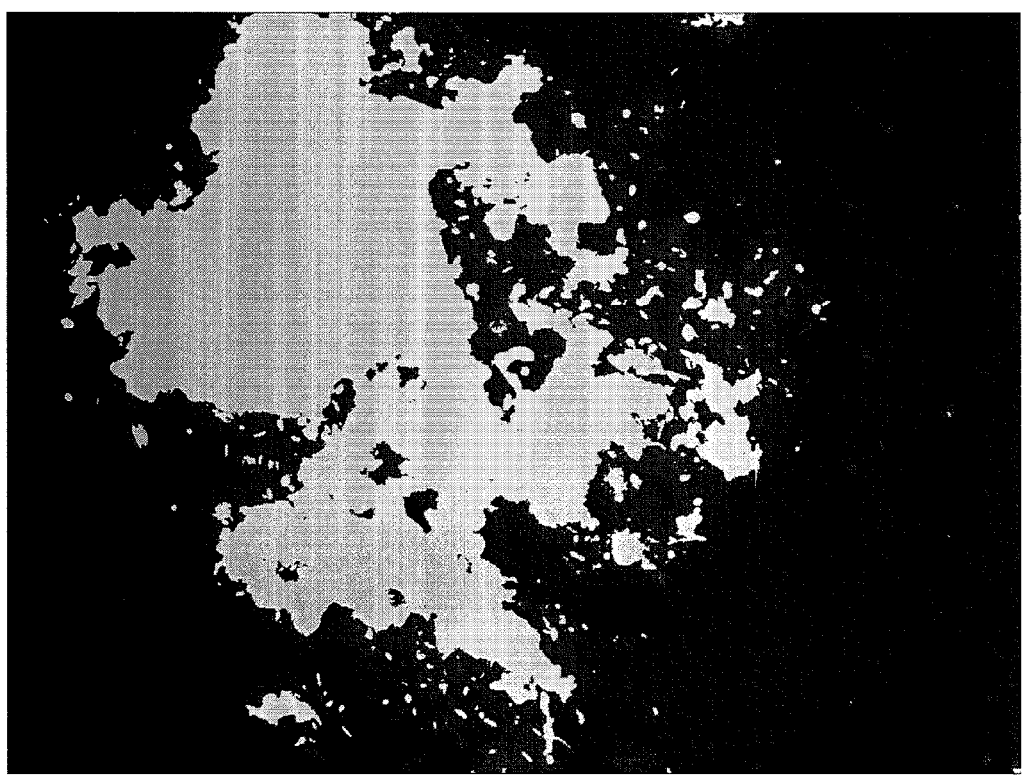
FIG. 36 is a CFDA binarized image of the same sample used in FIG. 35.
Figure 37:
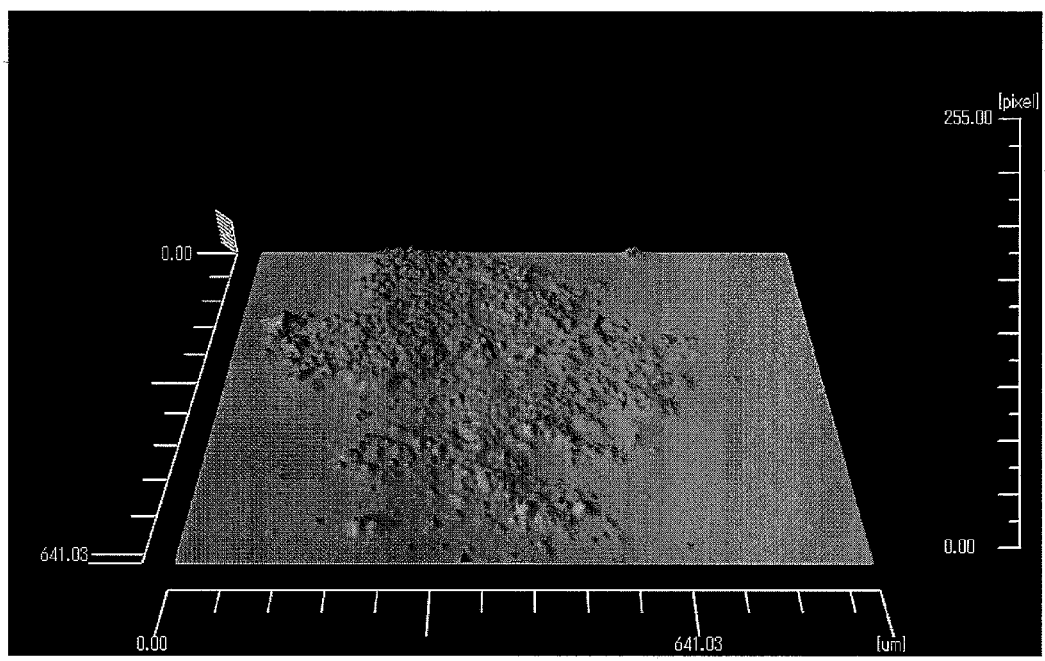
FIG. 37 is an image for the measurement of the total amount of PI fluorescence of the same sample used in FIG. 35.
Figure 38:
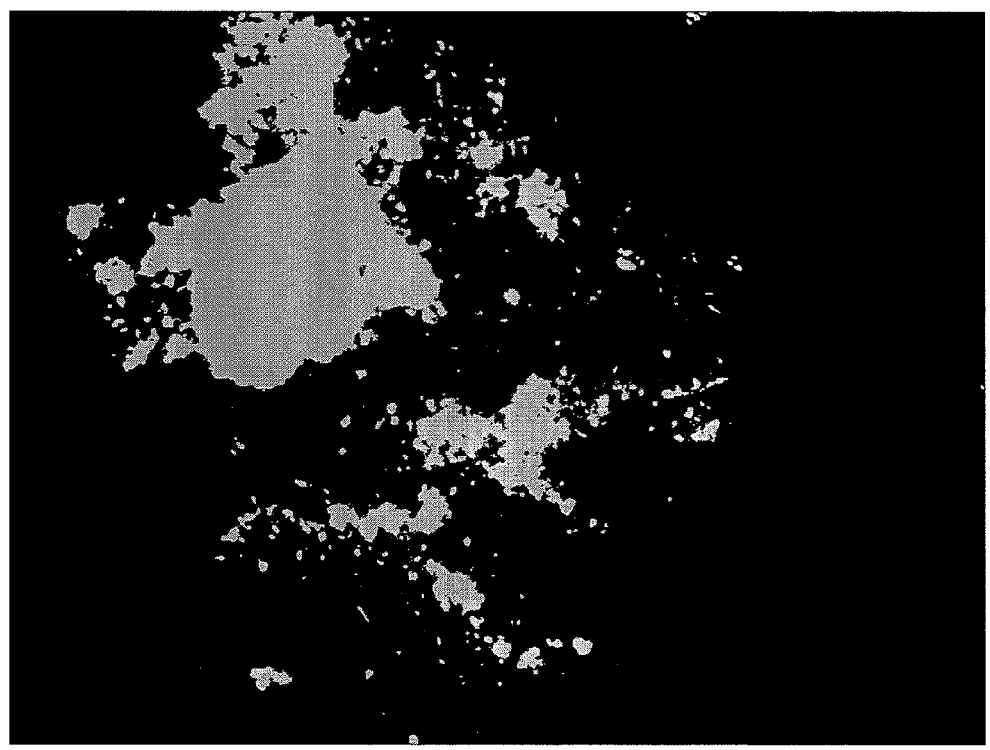
FIG. 38 is a PI binarized image of the same sample used in FIG. 35.

Fluorescent microscopy observation was performed by collecting a biofilm from the above biofilm treatment facility. FIG. 35 is an image for the measurement of the total amount of CFDA fluorescence of a sample before the addition of a microbial preparation in Example 4, FIG. 36 is a CFDA binarized image of the same sample used in FIG. 35, FIG. 37 is an image for the measurement of the total amount of PI fluorescence of the same sample used in FIG. 35, and FIG. 38 is a PI binarized image of the same sample used in FIG. 35.

Concerning this sample, a PI signal area and a CFDA signal area were digitalized. In this sample, the value of a ratio PI signal area/CFDA signal area became 0.45, and it was deter-

TABLE 3

| Situation of addition of microbial preparation | CFDA | PI | PI/CFDA | Solids retention time (days) | Solids retention time of formula 1 | COD reduction rate improved value (%) | SV30 improved value (%) | MC003 (kg) |
|---|---|---|---|---|---|---|---|---|
| | | | | Signal area (pixel) | | | | |
| Before operation | 37879 | 21362 | 0.56 | 12.4 | 6 | | | |
| On 28th day after operation | 20258 | 18614 | 0.92 | 12.0 | 6 | +6 | 0 | 5.7 |
| On 70th day after operation | 34111 | 44677 | 1.31 | 6.2 | 5 | +4 | −6 | 5.7 |
| | | | | Total fluorescence amount (pixel × luminance) | | | | |
| Before operation | 4125002 | 2424377 | 0.59 | 12.4 | 6.1 | | | |
| On 28th day after operation | 1381232 | 1391078 | 1.01 | 12.0 | 5.9 | +6 | 0 | 5.7 |
| On 70th day after operation | 3133541 | 5493136 | 1.75 | 6.2 | 4.9 | +4 | −6 | 5.7 |

As shown in Table 3, in the sample on the 70th day after the operation, the value of the ratio PI signal area/CFDA signal area became 1.31, and thus a further improvement in the physiological state of the sludge-constituting microbial community was recognized and also an improvement (6%) in the value of SV30 was recognized.

Example 4

Improvement Example by the Addition of Microbial Preparation to Biofilm System

In a biofilm treatment facility of industrial wastewater, for the purpose of improving a COD reduction rate of treated mined that an improvement is required. A trial of an improvement was made by adding a microbial preparation to a biofilm treatment tank.

In the above biofilm treatment facility, a microbial preparation (SEIKO PMC under the trade name of MC-008) was added to a biofilm treatment tank for the purpose of improving the physiological state of an activated sludge. The amount of the microbial preparation was 5.4 kg/day.

On the 17th day after the addition of the microbial preparation, a biofilm was collected again and fluorescent microscopy observation was performed.

Figure 39:
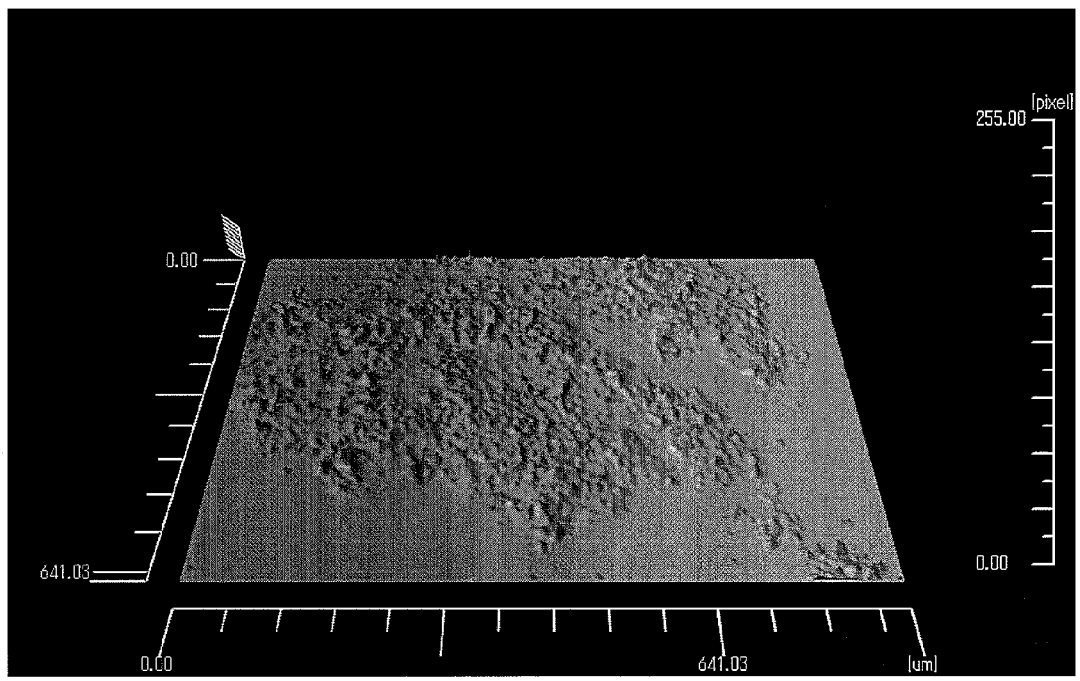
FIG. 39 is an image for the measurement of the total amount of CFDA fluorescence of a sample on the 17th day after the addition of a microbial preparation in Example 4.
Figure 40:
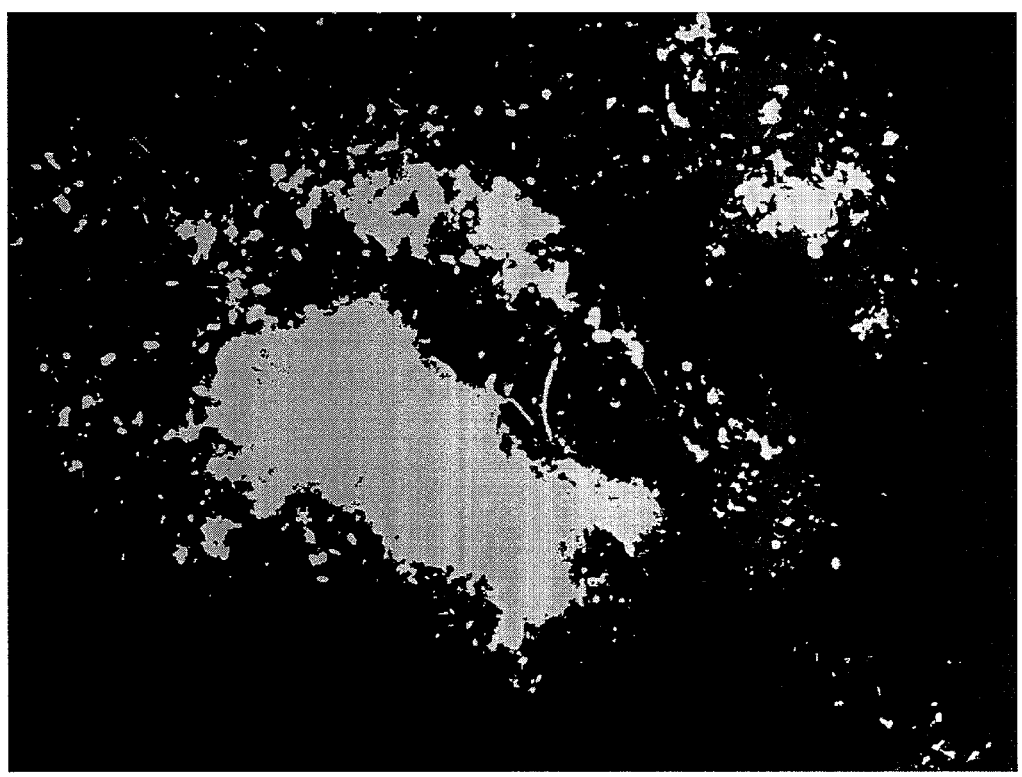
FIG. 40 is a CFDA binarized image of the same sample used in FIG. 39.
Figure 41:
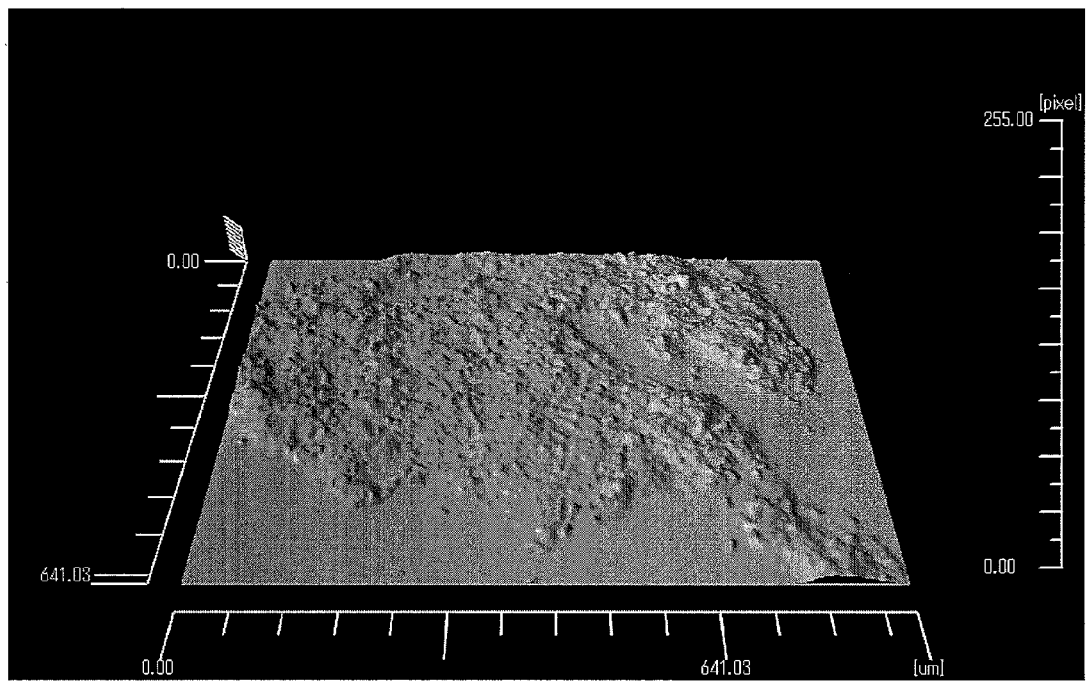
FIG. 41 is an image for the measurement of the total amount of PI fluorescence of the same sample used in FIG. 39.
Figure 42:
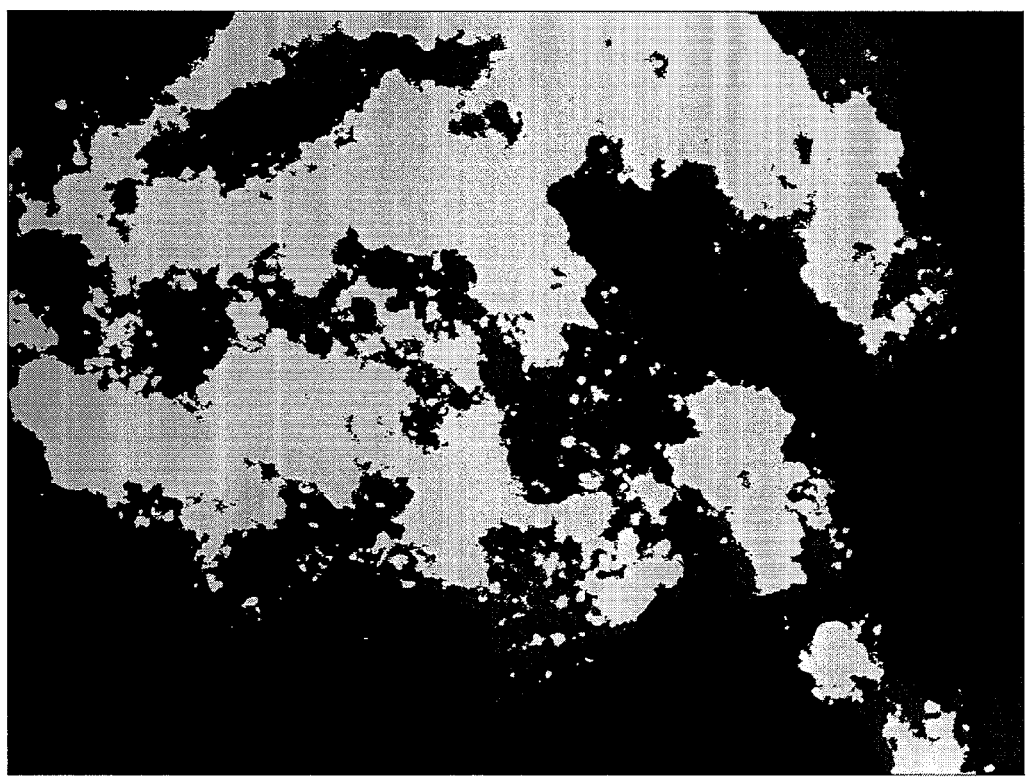
FIG. 42 is an image for the measurement of the total amount of PI fluorescence of the same sample used in FIG. 39.

In Table 4, digitized data of a fluorescent staining image of the activated sludge collected during a test period and an operation parameter of a treatment tank in Example 4 are shown. FIG. 39 is an image for the measurement of the total amount of CFDA fluorescence on the 17th day after the addition of a microbial preparation in Example 4, FIG. 40 is a CFDA binarized image of the same sample used in FIG. 39, and FIG. 41 is an image for the measurement of the total amount of PI fluorescence of the same sample used in FIG. 39. FIG. 42 is a PI binarized image of the same sample used in FIG. 39.

TABLE 4

| Situation of addition of microbial preparation | CFDA | PI | PI/CFDA | COD reduction rate improved value (%) | MC008 (Kg) |
|---|---|---|---|---|---|
| Signal area (pixel) | | | | | |
| Before addition | 164688 | 73983 | 0.45 | | 0 |
| On 17th day after addition | 87051 | 201327 | 2.31 | +27 | 5.4 |
| Total fluorescence amount (pixel × luminance) | | | | | |
| Before addition | 9029347 | 2521024 | 0.28 | | 0 |
| On 17th day after addition | 10255078 | 25833683 | 2.52 | +27 | 5.4 |

As shown in Table 4, in the sample on the 17th day after the addition, the value of the ratio PI signal area/CFDA signal area became 2.31 and a large change in the physiological state of the biofilm-constituting microbial community was recognized. Also, an improvement (27%) in a COD reduction rate of a treatment tank was recognized.

INDUSTRIAL APPLICABILITY

The method for determining the physiological state of a microbial community of the present invention can rapidly and precisely determine whether the physiological state of a microbial community present in a treatment tank of a wastewater biological treatment facility is satisfactory or not.

The wastewater treating method of the present invention can stably perform a wastewater treatment while maintaining and managing the physiological state of a microbe community satisfactorily, based on the physiological state of a microbial community determined by the determination method of the present invention.

The invention claimed is:

1. A method for treating a microbial community present in a treatment tank of a wastewater biological treatment facility, comprising the steps of:
   collecting the microbial community present in the treatment tank;
   staining the microbial community with a set of dyes consisting of a first fluorescent dye and a second fluorescent dye, wherein the first fluorescent dye which binds to a nucleotide chain of a microbe in the microbial community, and the second fluorescent dye is degraded by an enzyme in cells of the microbe to emit fluorescent light having a wavelength different from that of the first fluorescent dye;
   measuring a first fluorescent intensity (F1) derived from the first fluorescent dye and a second fluorescent intensity (F2) derived from the second fluorescent dye,
   calculating a value of a ratio (F1/F2) of the first fluorescent intensity (F1) to the second fluorescent intensity (F2);
   performing, when the ratio (F1/F2) calculated is less than 1 or more than 20, a wastewater treatment by either or both of:
   (A) placing a microbial preparation into a treatment tank, and
   (B) controlling a solids retention time of the treatment tank.

2. The method for determining the physiological state of a microbial community according to claim 1, wherein
   the first fluorescent dye is selected from the group consisting of propidium iodide, ethidium bromide, ethidium homodimer, DAPI, 7-aminoactinomycin D and SYTOX Green, and
   the second fluorescent dye is selected from the group consisting of fluorescein diacetate, carboxyfluorescein diacetate, sulfofluorescein diacetate, dichlorofluorescein diacetate, calcein-AM and CFSE.

3. The method for determining the physiological state of a microbial community according to claim 1, wherein the measuring of a fluorescent intensity is performed by fluorescent microscopy observation or analysis using a flow cytometer of the stained microbial community.

4. The method for determining the physiological state of a microbial community according to claim 1, wherein the measuring of a fluorescent intensity is performed by:
   observing the stained microbial community with a fluorescent microscope; digitalizing fluorescent light derived from the first fluorescent dye and the second fluorescent dye as a signal area based on a preset threshold of a signal intensity, of using an image processing software for an image of the fluorescent microscopy observation; and
   determining a value of a ratio of each signal area derived from the first fluorescent dye and the second fluorescent dye.

5. The method for determining the physiological state of a microbial community according to claim 1, wherein the measuring of a fluorescent intensity is performed by:
   observing the stained microbial community with a fluorescent microscope; calculating a luminance and a signal area regarding an image of the fluorescent microscopy observation using an image processing software;
   digitalizing a total fluorescence amount (=signal area×luminance) derived from a fluorescent dye; and
   determining a value of a ratio of the total fluorescence amount derived from the first fluorescent dye and the second fluorescent dye (S1/S2).

6. The method for determining the physiological state of a microbial community according to claim 1, wherein the measuring of a fluorescent intensity is performed by measuring the first fluorescent intensity (F1) and the second fluorescent intensity (F2) of the stained microbial community by use of a flow cytometer, and determining a value of a ratio of the first fluorescent intensity (F1) and the second fluorescent intensity (F2) (F1/F2).

7. The method for treating wastewater according to claim 1, wherein the (B) controlling a solids retention time of a treatment tank is performed by controlling the solids retention time of a treatment tank to be controlled to be within a solids retention time calculated by the following equation (1) ±2 days:

$$\text{solids retention time (day)} = (\tau \times X)/((a \times Ci) + (b \times Si) - (c \times \tau \times X)) \quad (1)$$

wherein each symbol in the equation (1) has the following meaning:
   $\tau$: hydraulic retention time of reaction tank V/Qi (days)
   Qi: wastewater amount (m$^3$/day)
   Ci: soluble BOD value of wastewater (mgO/L)
   Si: SS concentration of wastewater (mg/L)
   X: MLSS in reaction tank (mg/L)
   V: reaction tank volume (m$^3$)

a: sludge conversion rate relative to soluble BOD (gMLSS/gBOD)
b: sludge conversion rate relative to SS (gMLSS/gSS)
c: coefficient representing reduction amount due to endogenous respiration of activated sludge microbe (L/day).

8. The method for determining the physiological state of a microbial community according to claim 2, wherein the measuring of a fluorescent intensity is performed by fluorescent microscopy observation or analysis using a flow cytometer of the stained microbial community.

9. The method for determining the physiological state of a microbial community according to claim 2, wherein the measuring of a fluorescent intensity is performed by observing the stained microbial community with a fluorescent microscope;
digitalizing fluorescent light derived from the first fluorescent dye and the second fluorescent dye as a signal area based on a preset threshold of a signal intensity using an image processing software for an image of the fluorescent microscopy observation; and
determining a value of a ratio of each signal area derived from the first fluorescent dye and the second fluorescent dye.

10. The method for determining the physiological state of a microbial community according to claim 3, wherein the measuring of a fluorescent intensity is performed by observing the stained microbial community with a fluorescent microscope;
digitalizing fluorescent light derived from the first fluorescent dye and the second fluorescent dye as a signal area based on a preset threshold of a signal intensity using an image processing software for an image of the fluorescent microscopy observation; and
determining a value of a ratio of each signal area derived from the first fluorescent dye and the second fluorescent dye.

11. The method for determining the physiological state of a microbial community according to claim 2, wherein the measuring of a fluorescent intensity is performed by observing the stained microbial community with a fluorescent microscope;
calculating a luminance and a signal area regarding an image of the fluorescent microscopy observation using image processing software;
digitalizing a total fluorescence amount (=signal area×luminance) derived from a fluorescent dye; and
determining a value of a ratio of the total fluorescence amount derived from the first fluorescent dye and the second fluorescent dye (S1/S2).

12. The method for determining the physiological state of a microbial community according to claim 3, wherein the measuring of a fluorescent intensity is performed by observing the stained microbial community with a fluorescent microscope;
calculating a luminance and a signal area regarding an image of the fluorescent microscopy observation using image processing software;
digitalizing a total fluorescence amount (=signal area×luminance) derived from a fluorescent dye; and
determining a value of a ratio of the total fluorescence amount derived from the first fluorescent dye and the second fluorescent dye (S1/S2).

13. The method for determining the physiological state of a microbial community according to claim 2, wherein the measuring of a fluorescent intensity is performed by measuring the first fluorescent intensity (F1) and the second fluorescent intensity (F2) of the stained microbial community using a flow cytometer, and determining a value of a ratio of the first fluorescent intensity (F1) and the second fluorescent intensity (F2) (F1/F2).

14. The method for determining the physiological state of a microbial community according to claim 3, wherein the measuring of a fluorescent intensity is performed by measuring the first fluorescent intensity (F1) and the second fluorescent intensity (F2) of the stained microbial community using a flow cytometer, and determining a value of a ratio of the first fluorescent intensity (F1) and the second fluorescent intensity (F2) (F1/F2).

15. A method for treating wastewater, comprising:
performing the method for determining the physiological state of a microbial community according to claim 4; and
further performing, when the physiological state of the microbial community is determined to be unsatisfactory, a wastewater treatment by either or both of:
(A) placing a microbial preparation into a treatment tank, and
(B) controlling a solids retention time of the treatment tank while adjusting the operation state of a treatment tank of a wastewater biological treatment facility so that the physiological state of a microbial community becomes satisfactory.

16. A method for treating wastewater, comprising:
performing the method for determining the physiological state of a microbial community according to claim 5; and
further performing, when the physiological state of the microbial community is determined to be unsatisfactory, a wastewater treatment by either or both of:
(A) placing a microbial preparation into a treatment tank, and
(B) controlling a solids retention time of the treatment tank while adjusting the operation state of a treatment tank of a wastewater biological treatment facility so that the physiological state of a microbial community becomes satisfactory.

17. A method for treating wastewater, comprising:
performing the method for determining the physiological state of a microbial community according to claim 6; and
further performing, when the physiological state of the microbial community is determined to be unsatisfactory by determination in the determination method, a wastewater treatment by either or both of:
(A) placing a microbial preparation into a treatment tank, and
(B) controlling a solids retention time of the treatment tank while adjusting the operation state of a treatment tank of a wastewater biological treatment facility so that the physiological state of a microbial community becomes satisfactory.

* * * * *